US008057492B2

(12) United States Patent  
Ortiz et al.

(10) Patent No.: US 8,057,492 B2
(45) Date of Patent: Nov. 15, 2011

(54) AUTOMATICALLY ADJUSTING BAND SYSTEM WITH MEMS PUMP

(75) Inventors: Mark S. Ortiz, Milford, OH (US); Daniel F. Dlugos, Jr., Middletown, OH (US); David N. Plescia, Cincinnati, OH (US); David C. Yates, West Chester, OH (US); Jason L. Harris, Mason, OH (US); Mark S. Zeiner, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 754 days.

(21) Appl. No.: 12/029,794

(22) Filed: Feb. 12, 2008

(65) Prior Publication Data

US 2009/0204131 A1 Aug. 13, 2009

(51) Int. Cl.
*A61B 17/08* (2006.01)
(52) U.S. Cl. ........................................ 606/151
(58) Field of Classification Search .......... 606/151, 606/201–202; 417/413.2, 413.1, 413.3, 322; 600/31, 37, 492, 499, 503
See application file for complete search history.

(56) References Cited

U.S. PATENT DOCUMENTS

| RE3,036 E | 7/1868 | Shunk |
| RE3,037 E | 7/1868 | Tucker |
| RE3,115 E | 9/1868 | Lewis |
| RE3,187 E | 11/1868 | Winchester |
| RE3,322 E | 3/1869 | Murch |
| 236,373 A | 1/1881 | Spilman |
| 322,388 A | 7/1885 | Lord |
| 400,401 A | 3/1889 | Gutzkow |
| D23,637 S | 9/1894 | Casad |
| D24,900 S | 11/1895 | Clemecet |
| D25,318 S | 3/1896 | Perky |
| D27,151 S | 6/1897 | Moulten |
| D29,715 S | 11/1898 | Wheeler |

(Continued)

FOREIGN PATENT DOCUMENTS

CA 1059035 7/1979

(Continued)

OTHER PUBLICATIONS

"Application Specific Integrated Circuits (ASICs)", Honeywell product information from website http://www.honeywell.com/sites/portal?smap=aerospace&page=Radiation-Hardened-Electronics3&theme=T18&catID=CE06BEF88-65F8-6A1E-4ED1-6A1EC1B7AE7A&id=HA0E380D3-C27B-9EBF-AAC8-9FAF8851256D&sel=1&sel4=1; 1 page.

(Continued)

*Primary Examiner* — Melanie Tyson
*Assistant Examiner* — Son Dang
(74) *Attorney, Agent, or Firm* — Nutter McClennen & Fish LLP

(57) ABSTRACT

Devices and methods for forming a restriction in a patient are disclosed. In one exemplary embodiment, a restriction system is provided including an implantable restriction device, an implantable port in fluid communication with the implantable restriction device, and an implantable pump in fluid communication with the restriction device. In general, the implantable restriction device is adjustable and configured to form a restriction in a patient, and the implantable port is configured to receive fluid from a fluid source external to the patient. The implantable pump is a micro-electro-mechanical systems (MEMS) device effective to create pumping action to move fluid through the pump.

13 Claims, 8 Drawing Sheets

U.S. PATENT DOCUMENTS

| | | |
|---|---|---|
| D29,745 S | 11/1898 | Bunker |
| D29,885 S | 12/1898 | Gillespie et al. |
| D30,690 S | 5/1899 | Schwedtmann |
| D30,966 S | 6/1899 | Howe |
| D31,230 S | 7/1899 | Hogan |
| 689,758 A | 12/1901 | Shaw |
| 724,913 A | 4/1903 | Montgomery |
| 899,477 A | 9/1908 | Williams |
| 926,197 A | 6/1909 | Kim |
| 953,875 A | 4/1910 | Waring |
| 991,192 A | 5/1911 | Batttenfeld |
| 1,087,988 A | 2/1914 | Sheldon |
| 1,210,701 A | 1/1917 | Ryden |
| 1,219,296 A | 3/1917 | Hahn |
| 1,224,355 A | 5/1917 | Brown |
| 1,263,914 A | 4/1918 | Martin |
| 1,310,290 A | 7/1919 | Piechowicz |
| 1,384,873 A | 7/1921 | Strickland |
| 1,421,507 A | 7/1922 | Lindberg |
| 1,551,525 A | 8/1925 | Hamer |
| 1,560,973 A | 11/1925 | Cheron |
| 1,620,633 A | 3/1927 | Colvin |
| 1,623,403 A | 4/1927 | Friel |
| 1,689,085 A | 10/1928 | Russell et al. |
| 1,764,071 A | 6/1930 | Foulke |
| 1,782,704 A | 11/1930 | Woodruff |
| 1,807,107 A | 5/1931 | Sternberch |
| 1,865,446 A | 7/1932 | Sears |
| 1,882,338 A | 10/1932 | Reed et al. |
| 1,924,781 A | 8/1933 | Gaiser |
| 2,027,875 A | 1/1936 | Odend'hal |
| 2,063,430 A | 12/1936 | Graser |
| 2,099,160 A | 11/1937 | Charch |
| 2,105,127 A | 1/1938 | Petrone |
| 2,106,192 A | 1/1938 | Saville |
| 2,143,429 A | 1/1939 | Auble |
| 2,166,603 A | 7/1939 | Menzer |
| 2,168,427 A | 8/1939 | McConkey |
| 2,174,525 A | 10/1939 | Padernal |
| 2,177,564 A | 10/1939 | Havill |
| 2,178,463 A | 10/1939 | Bahnson |
| 2,180,599 A | 11/1939 | Menasco |
| 2,203,460 A | 6/1940 | Fieber |
| 2,206,038 A | 7/1940 | Lang Ford |
| 2,216,374 A | 10/1940 | Martin |
| 2,223,699 A | 12/1940 | Norgren |
| 2,225,145 A | 12/1940 | Baumbach |
| 2,225,880 A | 12/1940 | Montelius |
| 2,261,060 A | 10/1941 | Giesler |
| 2,261,355 A | 11/1941 | Flynn |
| 2,295,539 A | 9/1942 | Beach |
| 2,303,108 A | 11/1942 | Blackburn |
| 2,303,502 A | 12/1942 | Rous |
| 2,318,819 A | 5/1943 | Verson |
| 2,327,407 A | 8/1943 | Edyvean |
| 2,327,615 A | 8/1943 | Ankarlo |
| 2,354,571 A | 7/1944 | Blain |
| 2,426,392 A | 8/1947 | Fennema |
| 2,426,817 A | 9/1947 | Charlton et al. |
| 2,440,260 A | 4/1948 | Gall |
| 2,442,573 A | 6/1948 | Stafford |
| 2,453,217 A | 11/1948 | Gregg et al. |
| 2,455,859 A | 12/1948 | Foley |
| 2,477,922 A | 8/1949 | Emery et al. |
| 2,478,876 A | 8/1949 | Nelson |
| 2,482,392 A | 9/1949 | Whitaker |
| 2,494,881 A | 1/1950 | Kost |
| 2,509,210 A | 5/1950 | Clark |
| 2,509,673 A | 5/1950 | Church |
| 2,511,765 A | 6/1950 | Bradbury |
| 2,520,056 A | 8/1950 | Pozun |
| 2,521,976 A | 9/1950 | Hays |
| 2,533,924 A | 12/1950 | Foley |
| 2,538,259 A | 1/1951 | Merriman |
| 2,581,479 A | 1/1952 | Grashman |
| 2,600,324 A | 6/1952 | Rappaport |
| 2,606,003 A | 8/1952 | McNeill |
| 2,615,940 A | 10/1952 | Williams |
| 2,632,447 A | 3/1953 | Dobes |
| 2,639,342 A | 5/1953 | Cope |
| 2,640,119 A | 5/1953 | Bradford, Jr. |
| 2,641,742 A | 6/1953 | Wolfe |
| 2,651,304 A | 9/1953 | Browner |
| 2,665,577 A | 1/1954 | Sanowskis |
| 2,673,999 A | 4/1954 | Shey |
| 2,676,609 A | 4/1954 | Pfarrer |
| 2,684,118 A | 7/1954 | Osmun |
| 2,689,611 A | 9/1954 | Martinson |
| 2,697,435 A | 12/1954 | Ray |
| 2,723,323 A | 11/1955 | Niemi |
| 2,734,992 A | 2/1956 | Elliot et al. |
| 2,740,007 A | 3/1956 | Amelang |
| 2,740,853 A | 4/1956 | Hatman, Jr. |
| 2,742,323 A | 4/1956 | Shey |
| 2,747,332 A | 5/1956 | Morehouse |
| 2,753,876 A | 7/1956 | Kurt |
| 2,756,883 A | 7/1956 | Schreck |
| 2,756,983 A | 7/1956 | Furcini |
| 2,761,603 A | 9/1956 | Fairchild |
| 2,773,312 A | 12/1956 | Peck |
| 2,783,728 A | 3/1957 | Hoffmann |
| 2,787,875 A | 4/1957 | Johnson |
| 2,793,379 A | 5/1957 | Moore |
| 2,795,460 A | 6/1957 | Bletcher |
| 2,804,514 A | 8/1957 | Peters |
| 2,822,113 A | 2/1958 | Joiner, Jr. |
| 2,831,478 A | 4/1958 | Uddenberg et al. |
| 2,864,393 A | 12/1958 | Drake |
| 2,865,541 A | 12/1958 | Hicks |
| 2,870,024 A | 1/1959 | McK. Martin |
| 2,883,995 A | 4/1959 | Bialous et al. |
| 2,886,355 A | 5/1959 | Wurzel |
| 2,895,215 A | 7/1959 | Neher et al. |
| 2,899,493 A | 8/1959 | Levine |
| 2,902,861 A | 9/1959 | Frost et al. |
| 2,923,531 A | 2/1960 | Bauer et al. |
| 2,924,263 A | 2/1960 | Landis |
| 2,924,432 A | 2/1960 | Arps et al. |
| 2,930,170 A | 3/1960 | Holsman et al. |
| 2,938,592 A | 5/1960 | Charske et al. |
| 2,941,338 A | 6/1960 | Santschi |
| 2,943,682 A | 7/1960 | Ingram, Jr. et al. |
| 2,958,781 A | 11/1960 | Marchal et al. |
| 2,961,479 A | 11/1960 | Bertling |
| 2,976,355 A | 3/1961 | Levine |
| 2,976,686 A | 3/1961 | Stelzer |
| 2,977,876 A | 4/1961 | Meyers |
| 2,986,715 A | 5/1961 | Church et al. |
| 2,989,019 A | 6/1961 | Van Sciver, II |
| 3,010,692 A | 11/1961 | Jentoft |
| 3,013,234 A | 12/1961 | Bourns |
| 3,018,791 A | 1/1962 | Knox |
| 3,034,356 A | 5/1962 | Bieganski |
| 3,040,800 A | 6/1962 | Hartley |
| 3,054,618 A | 9/1962 | Abrams et al. |
| 3,060,262 A | 10/1962 | Hoer |
| 3,070,373 A | 12/1962 | Mathews et al. |
| 3,082,414 A | 3/1963 | Papaminas |
| 3,085,577 A | 4/1963 | Berman et al. |
| 3,096,410 A | 7/1963 | Anderson |
| 3,099,262 A | 7/1963 | Bigliano |
| 3,125,028 A | 3/1964 | Rohde |
| 3,126,029 A | 3/1964 | Englesson |
| 3,129,072 A | 4/1964 | Cook et al. |
| 3,135,914 A | 6/1964 | Callan et al. |
| 3,144,017 A | 8/1964 | Muth |
| 3,151,258 A | 9/1964 | Sonderegger et al. |
| 3,153,460 A | 10/1964 | Raskin |
| 3,161,051 A | 12/1964 | Perry, Jr. |
| 3,167,044 A | 1/1965 | Henrickson |
| 3,171,549 A | 3/1965 | Orloff |
| 3,172,700 A | 3/1965 | Haas |
| 3,173,269 A | 3/1965 | Imbertson |
| 3,182,494 A | 5/1965 | Beatty et al. |
| 3,187,181 A | 6/1965 | Keller |
| 3,187,745 A | 6/1965 | Baum et al. |
| 3,190,388 A | 6/1965 | Moser et al. |

| | | |
|---|---|---|
| 3,205,547 A | 9/1965 | Riekse |
| 3,208,255 A | 9/1965 | Burk |
| 3,209,570 A | 10/1965 | Hills |
| 3,221,468 A | 12/1965 | Casey |
| 3,228,703 A | 1/1966 | Wilson |
| 3,229,684 A | 1/1966 | Nagumo et al. |
| 3,236,088 A | 2/1966 | Moller |
| 3,238,624 A | 3/1966 | McCabe |
| 3,240,510 A | 3/1966 | Spouge |
| 3,245,642 A | 4/1966 | Dicke |
| 3,255,568 A | 6/1966 | Martin et al. |
| 3,260,091 A | 7/1966 | Shaw, Jr. |
| 3,265,822 A | 8/1966 | Moulten |
| 3,266,487 A | 8/1966 | Watkins et al. |
| 3,273,447 A | 9/1966 | Frank |
| 3,283,352 A | 11/1966 | Hu |
| 3,290,919 A | 12/1966 | Malinak et al. |
| 3,292,493 A | 12/1966 | Franklin |
| 3,292,888 A | 12/1966 | Fischer |
| 3,294,988 A | 12/1966 | Packard |
| 3,299,603 A | 1/1967 | Shaw |
| 3,299,882 A | 1/1967 | Masino |
| 3,301,514 A | 1/1967 | Sugaya |
| 3,302,457 A | 2/1967 | Mayes |
| 3,306,384 A | 2/1967 | Ross |
| 3,313,314 A | 4/1967 | Burke et al. |
| 3,316,935 A | 5/1967 | Kaiser et al. |
| 3,320,750 A | 5/1967 | Haise et al. |
| 3,321,035 A | 5/1967 | Tarpley |
| 3,332,788 A | 7/1967 | Barnby |
| 3,334,510 A | 8/1967 | Hallesy |
| 3,339,401 A | 9/1967 | Peters |
| 3,340,868 A | 9/1967 | Darling |
| 3,347,162 A | 10/1967 | Braznell |
| 3,350,944 A | 11/1967 | De Michele |
| 3,353,364 A | 11/1967 | Blanding et al. |
| 3,353,481 A | 11/1967 | Antonucci |
| 3,356,334 A | 12/1967 | Scaramucci |
| 3,356,510 A | 12/1967 | Barnby |
| 3,357,218 A | 12/1967 | Mitchell |
| 3,357,461 A | 12/1967 | Friendship |
| 3,359,741 A | 12/1967 | Nelson |
| 3,361,300 A | 1/1968 | Kaplan |
| 3,364,929 A | 1/1968 | Ide et al. |
| 3,365,684 A | 1/1968 | Stemke |
| 3,378,456 A | 4/1968 | Roberts |
| 3,380,445 A | 4/1968 | Frasier |
| 3,380,649 A | 4/1968 | Roberts |
| 3,385,022 A | 5/1968 | Anderson |
| 3,389,355 A | 6/1968 | Schroeder, Jr. |
| 3,393,612 A | 7/1968 | Gorgens et al. |
| 3,396,561 A | 8/1968 | Day |
| 3,399,667 A | 9/1968 | Nishimoto et al. |
| 3,400,734 A | 9/1968 | Rosenberg |
| 3,403,237 A | 9/1968 | Wysong |
| 3,409,924 A | 11/1968 | Slama |
| 3,411,347 A | 11/1968 | Wirth et al. |
| 3,417,476 A | 12/1968 | Martens |
| 3,420,325 A | 1/1969 | McAlister et al. |
| 3,422,324 A | 1/1969 | Webb |
| 3,426,165 A | 2/1969 | Beaman |
| 3,438,391 A | 4/1969 | Yocum |
| 3,443,608 A | 5/1969 | Copping et al. |
| 3,445,335 A | 5/1969 | Gluntz |
| 3,447,281 A | 6/1969 | Bufford et al. |
| 3,450,153 A | 6/1969 | Hildebrandt et al. |
| 3,453,546 A | 7/1969 | Fryer |
| 3,453,848 A | 7/1969 | Williamson |
| 3,456,134 A | 7/1969 | Ko |
| 3,457,909 A | 7/1969 | Laird |
| 3,460,557 A | 8/1969 | Gallant |
| 3,463,338 A | 8/1969 | Schneider |
| 3,469,818 A | 9/1969 | Cowan |
| 3,470,725 A | 10/1969 | Brown et al. |
| 3,472,230 A | 10/1969 | Fogarty |
| 3,478,344 A | 11/1969 | Schwitzgebel et al. |
| 3,482,449 A | 12/1969 | Werner |
| 3,482,816 A | 12/1969 | Arnold |
| 3,487,959 A | 1/1970 | Pearne et al. |
| 3,491,842 A | 1/1970 | Delacour et al. |
| 3,492,638 A | 1/1970 | Lane |
| 3,502,829 A | 3/1970 | Reynolds |
| 3,503,116 A | 3/1970 | Strack |
| 3,504,664 A | 4/1970 | Haddad |
| 3,505,808 A | 4/1970 | Eschle |
| 3,509,754 A | 5/1970 | Massingill et al. |
| 3,512,517 A | 5/1970 | Kadish et al. |
| 3,514,919 A | 6/1970 | Ashton et al. |
| 3,516,220 A | 6/1970 | Buford et al. |
| 3,517,553 A | 6/1970 | Williams et al. |
| 3,527,226 A | 9/1970 | Hakin et al. |
| 3,529,908 A | 9/1970 | Smith |
| 3,530,449 A | 9/1970 | Anderson |
| 3,533,403 A | 10/1970 | Woodson |
| 3,534,728 A | 10/1970 | Barrows |
| 3,534,872 A | 10/1970 | Roth et al. |
| 3,535,914 A | 10/1970 | Veith et al. |
| 3,539,009 A | 11/1970 | Kudlaty |
| 3,543,744 A | 12/1970 | LePar |
| 3,545,275 A | 12/1970 | Harrison et al. |
| 3,550,583 A | 12/1970 | Chiku |
| 3,550,847 A | 12/1970 | Scott |
| 3,563,094 A | 2/1971 | Rieschel |
| 3,563,245 A | 2/1971 | McLean et al. |
| 3,566,083 A | 2/1971 | McMillin |
| 3,566,875 A | 3/1971 | Stoehr |
| 3,568,367 A | 3/1971 | Myers |
| 3,568,636 A | 3/1971 | Lockwood |
| 3,576,554 A | 4/1971 | Temps, Jr. et al. |
| 3,580,082 A | 5/1971 | Strack |
| 3,581,402 A | 6/1971 | London et al. |
| 3,583,387 A | 6/1971 | Garner et al. |
| 3,587,204 A | 6/1971 | George |
| 3,590,809 A | 7/1971 | London |
| 3,590,818 A | 7/1971 | Lemole |
| 3,590,992 A | 7/1971 | Soderstrom et al. |
| 3,592,183 A | 7/1971 | Watkins et al. |
| 3,594,519 A | 7/1971 | Schmidlin |
| 3,602,885 A | 8/1971 | Grajeda |
| 3,610,016 A | 10/1971 | Bultman |
| 3,610,851 A | 10/1971 | Krupski |
| 3,611,811 A | 10/1971 | Lissau |
| 3,614,926 A | 10/1971 | Brechtel |
| 3,614,955 A | 10/1971 | Mirowski et al. |
| 3,619,742 A | 11/1971 | Rud, Jr. |
| 3,623,371 A | 11/1971 | Jullien-Davin |
| 3,624,854 A | 12/1971 | Strong |
| 3,630,242 A | 12/1971 | Schieser et al. |
| 3,631,847 A | 1/1972 | Hobbs, II |
| 3,633,881 A | 1/1972 | Yurdin |
| 3,635,061 A | 1/1972 | Rydell et al. |
| 3,635,074 A | 1/1972 | Moos et al. |
| 3,638,496 A | 2/1972 | King |
| 3,644,883 A | 2/1972 | Borman et al. |
| 3,648,687 A | 3/1972 | Ramsey, III |
| 3,651,289 A | 3/1972 | Nagashima et al. |
| 3,651,405 A | 3/1972 | Whitney et al. |
| 3,653,671 A | 4/1972 | Shipes |
| 3,659,615 A | 5/1972 | Enger |
| 3,677,685 A | 7/1972 | Aoki et al. |
| 3,686,958 A | 8/1972 | Porter et al. |
| 3,688,568 A | 9/1972 | Karper et al. |
| 3,701,392 A | 10/1972 | Wirth et al. |
| 3,702,677 A | 11/1972 | Heffington |
| 3,703,099 A | 11/1972 | Rouse et al. |
| 3,712,138 A | 1/1973 | Alinari et al. |
| 3,713,124 A | 1/1973 | Durland et al. |
| 3,719,524 A | 3/1973 | Ripley et al. |
| 3,721,412 A | 3/1973 | Kindorf |
| 3,723,247 A | 3/1973 | Leine et al. |
| 3,724,000 A | 4/1973 | Eakman |
| 3,727,463 A | 4/1973 | Intraub |
| 3,727,616 A | 4/1973 | Lenzkes |
| 3,730,174 A | 5/1973 | Madison |
| 3,730,560 A | 5/1973 | Abildgaard et al. |
| 3,731,679 A | 5/1973 | Wilhelmson et al. |
| 3,731,681 A | 5/1973 | Blackshear et al. |
| 3,732,731 A | 5/1973 | Fussell, Jr. |

| Patent No. | Date | Name |
|---|---|---|
| 3,735,040 A | 5/1973 | Punt et al. |
| 3,736,930 A | 6/1973 | Georgi |
| 3,738,356 A | 6/1973 | Workman |
| 3,740,921 A | 6/1973 | Meyer et al. |
| 3,746,111 A | 7/1973 | Berthiaume et al. |
| 3,748,678 A | 7/1973 | Ballou |
| 3,749,098 A | 7/1973 | De Bennetot et al. |
| 3,749,422 A | 7/1973 | Abildgaard et al. |
| 3,749,423 A | 7/1973 | Abildgaard et al. |
| 3,750,194 A | 8/1973 | Summers |
| 3,757,770 A | 9/1973 | Brayshaw et al. |
| 3,759,095 A | 9/1973 | Short, Jr. et al. |
| 3,760,638 A | 9/1973 | Lawson et al. |
| 3,763,960 A | 10/1973 | John et al. |
| 3,765,142 A | 10/1973 | Lindquist et al. |
| 3,765,494 A | 10/1973 | Kielman, Jr. |
| 3,769,156 A | 10/1973 | Brecy et al. |
| 3,769,830 A | 11/1973 | Porter et al. |
| 3,774,243 A | 11/1973 | Ng et al. |
| 3,776,333 A | 12/1973 | Mathauser |
| 3,778,051 A | 12/1973 | Allen et al. |
| 3,780,578 A | 12/1973 | Sellman et al. |
| 3,781,902 A | 12/1973 | Shim et al. |
| 3,783,585 A | 1/1974 | Hoyland et al. |
| 3,789,667 A | 2/1974 | Porter et al. |
| 3,796,095 A | 3/1974 | Fussell, Jr. |
| 3,807,219 A | 4/1974 | Wallskog |
| 3,811,429 A | 5/1974 | Fletcher et al. |
| 3,815,722 A | 6/1974 | Sessoms |
| 3,818,765 A | 6/1974 | Eriksen et al. |
| 3,820,400 A | 6/1974 | Russo |
| 3,820,795 A | 6/1974 | Taylor |
| 3,823,610 A | 7/1974 | Fussell, Jr. |
| 3,825,065 A | 7/1974 | Lloyd et al. |
| 3,825,963 A | 7/1974 | Abildgaard et al. |
| 3,825,964 A | 7/1974 | Groswith, III et al. |
| 3,828,672 A | 8/1974 | Gazzola et al. |
| 3,828,766 A | 8/1974 | Krasnow |
| 3,831,588 A | 8/1974 | Rindner |
| 3,831,942 A | 8/1974 | Del Mar |
| 3,833,238 A | 9/1974 | Liard et al. |
| 3,834,167 A | 9/1974 | Tabor |
| 3,834,739 A | 9/1974 | Abildgaard et al. |
| 3,835,523 A | 9/1974 | Stansfield et al. |
| 3,839,708 A | 10/1974 | Bredesen et al. |
| 3,842,483 A | 10/1974 | Cramer |
| 3,842,668 A | 10/1974 | Lippke et al. |
| 3,845,664 A | 11/1974 | Perry, Jr. |
| 3,845,751 A | 11/1974 | Runstetler |
| 3,845,757 A | 11/1974 | Weyer |
| 3,847,434 A | 11/1974 | Weman et al. |
| 3,850,208 A | 11/1974 | Hamilton |
| 3,853,117 A | 12/1974 | Murr |
| 3,854,469 A | 12/1974 | Giori et al. |
| 3,855,902 A | 12/1974 | Kirst et al. |
| 3,857,399 A | 12/1974 | Zacouto et al. |
| 3,857,452 A | 12/1974 | Hartman |
| 3,857,745 A | 12/1974 | Grausch et al. |
| 3,858,581 A | 1/1975 | Kamen |
| 3,863,622 A | 2/1975 | Buuck |
| 3,863,933 A | 2/1975 | Tredway |
| 3,867,950 A | 2/1975 | Fischell |
| 3,868,008 A | 2/1975 | Brumbaugh |
| 3,868,679 A | 2/1975 | Arneson |
| 3,871,599 A | 3/1975 | Takada et al. |
| 3,872,285 A | 3/1975 | Shum et al. |
| 3,874,388 A | 4/1975 | King et al. |
| 3,876,980 A | 4/1975 | Haemmig et al. |
| 3,878,908 A | 4/1975 | Andersson et al. |
| 3,881,528 A | 5/1975 | Mackenzie |
| 3,893,111 A | 7/1975 | Cotter |
| 3,893,451 A | 7/1975 | Durand et al. |
| 3,895,681 A | 7/1975 | Griffin et al. |
| 3,899,862 A | 8/1975 | Muys et al. |
| 3,904,234 A | 9/1975 | Hill et al. |
| 3,908,334 A | 9/1975 | Rychiger et al. |
| 3,908,461 A | 9/1975 | Turpen |
| 3,908,721 A | 9/1975 | McGahey et al. |
| 3,910,087 A | 10/1975 | Jones |
| 3,912,168 A | 10/1975 | Mullins et al. |
| 3,912,304 A | 10/1975 | Abildgaard et al. |
| 3,918,286 A | 11/1975 | Whitehead |
| 3,918,291 A | 11/1975 | Pauly et al. |
| 3,920,965 A | 11/1975 | Sohrwardy et al. |
| 3,921,682 A | 11/1975 | McGahey et al. |
| 3,922,951 A | 12/1975 | Linsinger et al. |
| 3,923,060 A | 12/1975 | Ellinwood, Jr. |
| 3,924,635 A | 12/1975 | Hakim et al. |
| 3,928,980 A | 12/1975 | Ganzinotti et al. |
| 3,929,175 A | 12/1975 | Coone |
| 3,930,682 A | 1/1976 | Booth |
| 3,930,852 A | 1/1976 | Tanaka et al. |
| 3,936,028 A | 2/1976 | Norton et al. |
| 3,940,122 A | 2/1976 | Janzen et al. |
| 3,940,630 A | 2/1976 | Bergonz |
| 3,942,299 A | 3/1976 | Bory et al. |
| 3,942,382 A | 3/1976 | Hok et al. |
| 3,942,516 A | 3/1976 | Glynn et al. |
| 3,942,536 A | 3/1976 | Mirowski et al. |
| 3,943,915 A | 3/1976 | Severson |
| 3,945,704 A | 3/1976 | Kraus et al. |
| 3,946,613 A | 3/1976 | Silver |
| 3,946,615 A | 3/1976 | Hluchan |
| 3,946,724 A | 3/1976 | La Balme et al. |
| 3,948,141 A | 4/1976 | Shinjo et al. |
| 3,949,388 A | 4/1976 | Fuller |
| 3,953,289 A | 4/1976 | Costes et al. |
| 3,954,271 A | 5/1976 | Tredway, Sr. |
| 3,958,558 A | 5/1976 | Dunphy et al. |
| 3,961,425 A | 6/1976 | Swanson et al. |
| 3,961,646 A | 6/1976 | Schon et al. |
| 3,962,895 A | 6/1976 | Rydell et al. |
| 3,962,921 A | 6/1976 | Lips |
| 3,963,019 A | 6/1976 | Quandt |
| 3,964,485 A | 6/1976 | Neumeier |
| 3,964,770 A | 6/1976 | Abildgaard et al. |
| 3,967,737 A | 7/1976 | Peralta et al. |
| 3,968,473 A | 7/1976 | Patton et al. |
| 3,968,694 A | 7/1976 | Clark |
| 3,972,320 A | 8/1976 | Kalman |
| 3,973,753 A | 8/1976 | Wheeler |
| 3,973,858 A | 8/1976 | Poisson et al. |
| 3,974,655 A | 8/1976 | Halpern et al. |
| 3,974,865 A | 8/1976 | Fenton et al. |
| 3,977,391 A | 8/1976 | Fleischmann |
| 3,980,871 A | 9/1976 | Lindstrom et al. |
| 3,982,571 A | 9/1976 | Fenton et al. |
| 3,983,948 A | 10/1976 | Jeter |
| 3,985,133 A | 10/1976 | Jenkins et al. |
| 3,987,860 A | 10/1976 | Jabsen |
| 3,989,005 A | 11/1976 | Bowler, Jr. et al. |
| 3,991,749 A | 11/1976 | Zent |
| 3,992,948 A | 11/1976 | D'Antonio et al. |
| 3,993,149 A | 11/1976 | Harvey |
| 3,996,927 A | 12/1976 | Frank |
| 3,996,962 A | 12/1976 | Sutherland |
| 4,003,141 A | 1/1977 | Le Roy |
| 4,005,282 A | 1/1977 | Jennings |
| 4,005,593 A | 2/1977 | Goldberg |
| 4,006,735 A | 2/1977 | Hittman et al. |
| 4,009,375 A | 2/1977 | White et al. |
| 4,009,591 A | 3/1977 | Hester |
| 4,010,449 A | 3/1977 | Faggin et al. |
| 4,014,319 A | 3/1977 | Favre et al. |
| 4,014,321 A | 3/1977 | March |
| 4,016,764 A | 4/1977 | Rice |
| 4,017,329 A | 4/1977 | Larson |
| 4,018,134 A | 4/1977 | Linsinger et al. |
| 4,022,190 A | 5/1977 | Meyer |
| 4,024,864 A | 5/1977 | Davies et al. |
| 4,025,912 A | 5/1977 | Rice |
| 4,026,276 A | 5/1977 | Chubbuck |
| 4,027,661 A | 6/1977 | Lyon et al. |
| 4,031,899 A | 6/1977 | Renirie et al. |
| 4,036,775 A | 7/1977 | Trautvetter et al. |
| 4,039,069 A | 8/1977 | Kwan et al. |
| 4,041,954 A | 8/1977 | Ohara et al. |
| 4,042,504 A | 8/1977 | Drori et al. |

| | | | | | |
|---|---|---|---|---|---|
| 4,045,345 A | 8/1977 | Drori et al. | 4,183,124 A | 1/1980 | Hoffman |
| 4,047,851 A | 9/1977 | Bender | 4,183,247 A | 1/1980 | Allen et al. |
| 4,048,494 A | 9/1977 | Liesting et al. | 4,185,641 A | 1/1980 | Minior et al. |
| 4,048,879 A | 9/1977 | Cox | 4,186,287 A | 1/1980 | Scott |
| 4,049,004 A | 9/1977 | Walters | 4,186,749 A | 2/1980 | Fryer |
| 4,051,338 A | 9/1977 | Harris, III | 4,186,751 A | 2/1980 | Fleischmann |
| 4,052,991 A | 10/1977 | Zacouto et al. | 4,190,057 A | 2/1980 | Hill et al. |
| 4,055,074 A | 10/1977 | Thimons et al. | 4,191,004 A | 3/1980 | Gmuer et al. |
| 4,055,175 A | 10/1977 | Clemens et al. | 4,191,187 A | 3/1980 | Wright et al. |
| 4,056,854 A | 11/1977 | Boretos et al. | 4,192,192 A | 3/1980 | Schnell |
| 4,058,007 A | 11/1977 | Exner et al. | 4,193,397 A | 3/1980 | Tucker et al. |
| 4,062,351 A | 12/1977 | Hastwell et al. | 4,204,547 A | 5/1980 | Allocca |
| 4,062,354 A | 12/1977 | Taylor et al. | 4,206,755 A | 6/1980 | Klein et al. |
| 4,062,360 A | 12/1977 | Bentley | 4,206,761 A | 6/1980 | Cosman |
| 4,063,439 A | 12/1977 | Besson et al. | 4,206,762 A | 6/1980 | Cosman |
| 4,064,882 A | 12/1977 | Johnson et al. | 4,207,903 A | 6/1980 | O'Neill |
| 4,070,239 A | 1/1978 | Bevilacqua | 4,212,074 A | 7/1980 | Kuno et al. |
| 4,072,047 A | 2/1978 | Reismuller et al. | 4,217,221 A | 8/1980 | Masso |
| 4,073,292 A | 2/1978 | Edelman | 4,217,588 A | 8/1980 | Freeny, Jr. |
| 4,075,099 A | 2/1978 | Pelton et al. | 4,220,189 A | 9/1980 | Marquez |
| 4,075,602 A | 2/1978 | Clothier | 4,221,219 A | 9/1980 | Tucker |
| 4,077,072 A | 3/1978 | Dezura et al. | 4,221,523 A | 9/1980 | Eberle |
| 4,077,394 A | 3/1978 | McCurdy | 4,222,377 A | 9/1980 | Burton |
| 4,077,405 A | 3/1978 | Haerten et al. | 4,223,837 A | 9/1980 | Gubbiotti et al. |
| 4,077,882 A | 3/1978 | Gangemi | 4,226,124 A | 10/1980 | Kersten et al. |
| 4,078,620 A | 3/1978 | Westlake et al. | 4,226,229 A | 10/1980 | Eckhart et al. |
| 4,080,653 A | 3/1978 | Barnes, Jr. et al. | 4,227,533 A | 10/1980 | Godfrey |
| 4,084,752 A | 4/1978 | Hagiwara et al. | 4,231,376 A | 11/1980 | Lyon et al. |
| 4,086,488 A | 4/1978 | Hill | 4,232,682 A | 11/1980 | Veth |
| 4,087,568 A | 5/1978 | Fay et al. | 4,237,900 A | 12/1980 | Schulman et al. |
| 4,088,417 A | 5/1978 | Kosmowski | 4,241,247 A | 12/1980 | Byrne et al. |
| 4,089,329 A | 5/1978 | Couvillon, Jr. et al. | 4,241,870 A | 12/1980 | Marcus |
| 4,090,802 A | 5/1978 | Bilz et al. | 4,245,593 A | 1/1981 | Stein |
| 4,092,719 A | 5/1978 | Salmon et al. | 4,246,877 A | 1/1981 | Kennedy |
| 4,092,925 A | 6/1978 | Fromson | 4,247,850 A | 1/1981 | Marcus |
| 4,096,866 A | 6/1978 | Fischell | 4,248,238 A | 2/1981 | Joseph et al. |
| 4,098,293 A | 7/1978 | Kramer et al. | 4,248,241 A | 2/1981 | Tacchi |
| 4,103,496 A | 8/1978 | Colamussi et al. | 4,256,094 A | 3/1981 | Kapp et al. |
| 4,106,370 A | 8/1978 | Kraus et al. | 4,256,118 A | 3/1981 | Nagel et al. |
| 4,107,689 A | 8/1978 | Jellinek | 4,262,343 A | 4/1981 | Claycomb |
| 4,107,995 A | 8/1978 | Ligman et al. | 4,262,632 A | 4/1981 | Hanton et al. |
| 4,108,148 A | 8/1978 | Cannon, III | 4,265,241 A | 5/1981 | Portner et al. |
| 4,108,575 A | 8/1978 | Schal et al. | 4,265,252 A | 5/1981 | Chubbuck et al. |
| 4,109,148 A | 8/1978 | Jaulmes et al. | 4,271,018 A | 6/1981 | Drori et al. |
| 4,109,518 A | 8/1978 | Dooley et al. | 4,273,070 A | 6/1981 | Hoefelmayr et al. |
| 4,109,644 A | 8/1978 | Kojima | 4,274,444 A | 6/1981 | Ruyak |
| 4,111,056 A | 9/1978 | Mastromatteo | 4,275,600 A | 6/1981 | Turner et al. |
| 4,111,629 A | 9/1978 | Nussbaumer et al. | 4,275,913 A | 6/1981 | Marcus |
| 4,114,424 A | 9/1978 | Johnson | 4,278,540 A | 7/1981 | Drori et al. |
| 4,114,606 A | 9/1978 | Seylar | 4,280,036 A | 7/1981 | Fukatsu et al. |
| 4,120,097 A | 10/1978 | Jeter | 4,280,775 A | 7/1981 | Wood |
| 4,120,134 A | 10/1978 | Scholle | 4,281,666 A | 8/1981 | Cosman |
| 4,121,635 A | 10/1978 | Hansel | 4,281,667 A | 8/1981 | Cosman |
| 4,123,310 A | 10/1978 | Varon et al. | 4,284,073 A | 8/1981 | Krause et al. |
| 4,124,023 A | 11/1978 | Fleischmann et al. | 4,285,770 A | 8/1981 | Chi et al. |
| 4,127,110 A | 11/1978 | Bullara | 4,291,699 A | 9/1981 | Geddes et al. |
| 4,130,169 A | 12/1978 | Denison | 4,295,963 A | 10/1981 | Drori et al. |
| 4,131,596 A | 12/1978 | Allen | 4,297,927 A | 11/1981 | Kuroda et al. |
| 4,133,355 A | 1/1979 | Mayer | 4,303,075 A | 12/1981 | Heilman et al. |
| 4,133,367 A | 1/1979 | Abell | 4,305,402 A | 12/1981 | Katims |
| 4,140,131 A | 2/1979 | Dutcher et al. | 4,312,374 A | 1/1982 | Drori et al. |
| 4,141,348 A | 2/1979 | Hittman | 4,314,480 A | 2/1982 | Becker |
| 4,141,349 A | 2/1979 | Ory et al. | 4,316,693 A | 2/1982 | Baxter et al. |
| 4,143,661 A | 3/1979 | LaForge et al. | 4,325,387 A | 4/1982 | Helfer |
| 4,146,029 A | 3/1979 | Ellinwood, Jr. | 4,327,804 A | 5/1982 | Reed |
| 4,147,161 A | 4/1979 | Ikebe et al. | 4,328,654 A | 5/1982 | Van Ginkel et al. |
| 4,148,096 A | 4/1979 | Haas et al. | 4,332,254 A | 6/1982 | Lundquist |
| 4,149,423 A | 4/1979 | Frosch et al. | 4,339,831 A | 7/1982 | Johnson |
| 4,151,823 A | 5/1979 | Grosse et al. | 4,342,218 A | 8/1982 | Fox |
| 4,153,085 A | 5/1979 | Adams | 4,342,308 A | 8/1982 | Trick |
| 4,156,422 A | 5/1979 | Hildebrandt et al. | 4,346,604 A | 8/1982 | Snook et al. |
| 4,160,448 A | 7/1979 | Jackson | 4,347,851 A | 9/1982 | Jundanian |
| 4,160,971 A | 7/1979 | Jones et al. | 4,350,647 A | 9/1982 | de la Cruz |
| 4,166,469 A | 9/1979 | Littleford | 4,350,970 A | 9/1982 | von Tomkewitsch et al. |
| 4,167,304 A | 9/1979 | Gelbke | 4,351,037 A | 9/1982 | Scherbatskoy |
| 4,167,952 A | 9/1979 | Reinicke | 4,351,116 A | 9/1982 | Scott, Jr. |
| 4,168,567 A | 9/1979 | Leguy et al. | 4,356,486 A | 10/1982 | Mount |
| 4,170,280 A | 10/1979 | Schwarz | 4,360,010 A | 11/1982 | Finney |
| 4,171,218 A | 10/1979 | Hoshino et al. | 4,360,277 A | 11/1982 | Daniel et al. |

| | | | | | | |
|---|---|---|---|---|---|---|
| 4,361,153 A | 11/1982 | Slocum et al. | | 4,492,632 A | 1/1985 | Mattson |
| 4,363,236 A | 12/1982 | Meyers | | 4,494,411 A | 1/1985 | Koschke et al. |
| 4,364,276 A | 12/1982 | Shimazoe et al. | | 4,494,950 A | 1/1985 | Fischell |
| 4,365,425 A | 12/1982 | Gotchel | | 4,497,176 A | 2/1985 | Rubin et al. |
| 4,368,937 A | 1/1983 | Palombo et al. | | 4,497,201 A | 2/1985 | Allen et al. |
| 4,369,013 A | 1/1983 | Abildgaard et al. | | 4,499,394 A | 2/1985 | Koal |
| 4,373,527 A | 2/1983 | Fischell | | 4,499,691 A | 2/1985 | Karazim et al. |
| 4,376,523 A | 3/1983 | Goyen et al. | | 4,499,750 A | 2/1985 | Gerber et al. |
| 4,378,809 A | 4/1983 | Cosman | | 4,503,678 A | 3/1985 | Wimbush et al. |
| 4,380,427 A | 4/1983 | Hehl et al. | | 4,511,974 A | 4/1985 | Nakane et al. |
| 4,385,636 A | 5/1983 | Cosman | | 4,513,295 A | 4/1985 | Jones et al. |
| 4,386,422 A | 5/1983 | Mumby et al. | | 4,515,004 A | 5/1985 | Jaenson |
| 4,387,907 A | 6/1983 | Hiestand et al. | | 4,515,750 A | 5/1985 | Pardini et al. |
| 4,392,368 A | 7/1983 | Folkesson et al. | | 4,516,866 A | 5/1985 | Yamauchi et al. |
| 4,393,899 A | 7/1983 | Tsuji et al. | | 4,518,637 A | 5/1985 | Takeda et al. |
| 4,393,951 A | 7/1983 | Horst-Rudolf et al. | | 4,519,401 A | 5/1985 | Ko et al. |
| 4,395,232 A | 7/1983 | Koch | | 4,520,443 A | 5/1985 | Yuki et al. |
| 4,395,258 A | 7/1983 | Wang et al. | | 4,522,213 A | 6/1985 | Wallroth et al. |
| 4,395,916 A | 8/1983 | Martin | | 4,527,568 A | 7/1985 | Rickards et al. |
| 4,398,983 A | 8/1983 | Suzuki et al. | | 4,529,401 A | 7/1985 | Leslie et al. |
| 4,399,705 A | 8/1983 | Weiger et al. | | 4,531,526 A | 7/1985 | Genest |
| 4,399,707 A | 8/1983 | Wamstad | | 4,531,936 A | 7/1985 | Gordon |
| 4,399,809 A | 8/1983 | Baro et al. | | 4,536,000 A | 8/1985 | Rohm et al. |
| 4,399,821 A | 8/1983 | Bowers | | 4,537,005 A | 8/1985 | Hoyland et al. |
| 4,403,984 A | 9/1983 | Ash et al. | | 4,537,129 A | 8/1985 | Heinemann et al. |
| 4,404,968 A | 9/1983 | Evans, Sr. | | 4,538,616 A | 9/1985 | Rogoff |
| 4,404,974 A | 9/1983 | Titus | | 4,540,404 A | 9/1985 | Wolvek |
| 4,405,318 A | 9/1983 | Whitney et al. | | 4,542,461 A | 9/1985 | Eldridge et al. |
| 4,407,125 A | 10/1983 | Parsons et al. | | 4,544,369 A | 10/1985 | Skakoon et al. |
| 4,407,271 A | 10/1983 | Schiff | | 4,545,185 A | 10/1985 | Chikatani et al. |
| 4,407,296 A | 10/1983 | Anderson | | 4,546,524 A | 10/1985 | Kreft |
| 4,407,326 A | 10/1983 | Wilhelm | | 4,548,209 A | 10/1985 | Wielders et al. |
| 4,408,597 A | 10/1983 | Tenney, Jr. | | 4,552,150 A | 11/1985 | Zacouto et al. |
| 4,408,615 A | 10/1983 | Grossman | | 4,553,226 A | 11/1985 | Scherbatskoy |
| 4,415,071 A | 11/1983 | Butler et al. | | 4,556,063 A | 12/1985 | Thompson et al. |
| 4,416,282 A | 11/1983 | Saulson et al. | | 4,557,269 A | 12/1985 | Reynolds et al. |
| 4,418,899 A | 12/1983 | Zimmermann et al. | | 4,557,332 A | 12/1985 | Denison et al. |
| 4,419,393 A | 12/1983 | Hanson et al. | | 4,559,815 A | 12/1985 | Needham et al. |
| 4,421,505 A | 12/1983 | Schwartz | | 4,560,979 A | 12/1985 | Rosskopf et al. |
| 4,424,720 A | 1/1984 | Bucchianeri | | 4,561,442 A | 12/1985 | Vollmann et al. |
| 4,428,228 A | 1/1984 | Banzhaf et al. | | 4,562,751 A | 1/1986 | Nason et al. |
| 4,428,365 A | 1/1984 | Hakky et al. | | 4,563,175 A | 1/1986 | LaFond |
| 4,430,899 A | 2/1984 | Wessel et al. | | 4,565,116 A | 1/1986 | Hehl et al. |
| 4,431,009 A | 2/1984 | Marino, Jr. et al. | | 4,566,456 A | 1/1986 | Koning et al. |
| 4,431,365 A | 2/1984 | Sturtz, Jr. | | 4,569,623 A | 2/1986 | Goldmann |
| 4,432,363 A | 2/1984 | Kakegawa et al. | | 4,570,351 A | 2/1986 | Szanto et al. |
| 4,435,173 A | 3/1984 | Siposs et al. | | 4,571,161 A | 2/1986 | Leblanc et al. |
| 4,439,186 A | 3/1984 | Kuhl et al. | | 4,571,995 A | 2/1986 | Timme |
| 4,441,491 A | 4/1984 | Evans, Sr. | | 4,573,835 A | 3/1986 | Eckardt et al. |
| 4,441,501 A | 4/1984 | Parent | | 4,574,792 A | 3/1986 | Trick |
| 4,444,194 A | 4/1984 | Burcham | | 4,576,181 A | 3/1986 | Wallace et al. |
| 4,444,498 A | 4/1984 | Heinemann | | 4,576,183 A | 3/1986 | Plicchi et al. |
| 4,445,385 A | 5/1984 | Endo | | 4,577,512 A | 3/1986 | Lowenheck et al. |
| 4,446,711 A | 5/1984 | Valente | | 4,581,018 A | 4/1986 | Jassawalla et al. |
| 4,447,224 A | 5/1984 | DeCant, Jr. et al. | | 4,581,915 A | 4/1986 | Haulsee et al. |
| 4,449,493 A | 5/1984 | Kopec et al. | | 4,587,840 A | 5/1986 | Dobler et al. |
| 4,450,811 A | 5/1984 | Ichikawa et al. | | 4,589,805 A | 5/1986 | Duffner et al. |
| 4,451,033 A | 5/1984 | Nestegard | | 4,592,339 A | 6/1986 | Kuzmak et al. |
| 4,453,537 A | 6/1984 | Spitzer | | 4,592,340 A | 6/1986 | Boyles |
| 4,453,578 A | 6/1984 | Wilder | | 4,593,703 A | 6/1986 | Cosman |
| 4,460,835 A | 7/1984 | Masuoka et al. | | 4,595,228 A | 6/1986 | Chu |
| 4,464,170 A | 8/1984 | Clemens et al. | | 4,596,563 A | 6/1986 | Pande |
| 4,465,015 A | 8/1984 | Osta et al. | | 4,599,943 A | 7/1986 | Kobler et al. |
| 4,465,474 A | 8/1984 | Mardorf et al. | | 4,600,855 A | 7/1986 | Strachan et al. |
| 4,466,290 A | 8/1984 | Frick | | 4,602,541 A | 7/1986 | Benzinger et al. |
| 4,468,172 A | 8/1984 | Dixon et al. | | 4,604,089 A | 8/1986 | Santangelo et al. |
| 4,468,762 A | 8/1984 | Jurgens et al. | | 4,605,354 A | 8/1986 | Daly |
| 4,469,365 A | 9/1984 | Marcus et al. | | 4,606,419 A | 8/1986 | Perini |
| 4,471,182 A | 9/1984 | Wielgos et al. | | 4,606,478 A | 8/1986 | Hack et al. |
| 4,471,786 A | 9/1984 | Inagaki et al. | | 4,610,256 A | 9/1986 | Wallace |
| 4,473,067 A | 9/1984 | Schiff | | 4,614,137 A | 9/1986 | Jones |
| 4,473,078 A | 9/1984 | Angel | | 4,617,016 A | 10/1986 | Blomberg et al. |
| 4,476,721 A | 10/1984 | Hochreuther et al. | | 4,618,861 A | 10/1986 | Gettens et al. |
| 4,478,213 A | 10/1984 | Redding | | 4,620,807 A | 11/1986 | Polit |
| 4,478,538 A | 10/1984 | Kakino et al. | | 4,621,331 A | 11/1986 | Iwata et al. |
| 4,483,196 A | 11/1984 | Kurtz et al. | | 4,622,871 A | 11/1986 | Van Sickle et al. |
| 4,484,135 A | 11/1984 | Ishihara et al. | | 4,626,462 A | 12/1986 | Kober et al. |
| 4,485,813 A | 12/1984 | Anderson et al. | | 4,633,304 A | 12/1986 | Nagasaki et al. |
| 4,489,916 A | 12/1984 | Stevens | | 4,633,878 A | 1/1987 | Bombardieri et al. |

| | | | | | | |
|---|---|---|---|---|---|---|
| 4,635,182 A | 1/1987 | Hintz | | 4,796,641 A | 1/1989 | Mills et al. |
| 4,637,736 A | 1/1987 | Andeen et al. | | 4,798,211 A | 1/1989 | Goor et al. |
| 4,638,665 A | 1/1987 | Benson et al. | | 4,798,227 A | 1/1989 | Goodwin |
| 4,644,246 A | 2/1987 | Knapen et al. | | 4,799,491 A | 1/1989 | Eckerle |
| 4,646,553 A | 3/1987 | Tufte et al. | | 4,799,625 A | 1/1989 | Weaver, Jr. et al. |
| 4,648,363 A | 3/1987 | Kronich | | 4,802,488 A | 2/1989 | Eckerle |
| 4,648,406 A | 3/1987 | Miller | | 4,803,987 A | 2/1989 | Calfee et al. |
| 4,658,358 A | 4/1987 | Leach et al. | | 4,804,368 A | 2/1989 | Skakoon et al. |
| 4,658,760 A | 4/1987 | Zebuhr | | 4,807,321 A | 2/1989 | Grasselli et al. |
| 4,660,568 A | 4/1987 | Cosman | | 4,808,167 A | 2/1989 | Mann et al. |
| 4,665,511 A | 5/1987 | Rodney et al. | | 4,812,823 A | 3/1989 | Dickerson |
| 4,665,896 A | 5/1987 | LaForge et al. | | 4,819,656 A | 4/1989 | Spector |
| 4,669,484 A | 6/1987 | Masters | | 4,820,265 A | 4/1989 | DeSatnick et al. |
| 4,672,974 A | 6/1987 | Lee | | 4,820,953 A | 4/1989 | Saubolle et al. |
| 4,674,457 A | 6/1987 | Berger et al. | | 4,821,167 A | 4/1989 | Wiebe |
| 4,674,546 A | 6/1987 | Fournier et al. | | 4,821,723 A | 4/1989 | Baker, Jr. et al. |
| 4,678,408 A | 7/1987 | Nason et al. | | 4,823,779 A | 4/1989 | Daly et al. |
| 4,681,559 A | 7/1987 | Hooven | | 4,830,006 A | 5/1989 | Haluska et al. |
| 4,683,850 A | 8/1987 | Bauder et al. | | 4,832,034 A | 5/1989 | Pizziconi et al. |
| 4,685,463 A | 8/1987 | Williams | | 4,833,384 A | 5/1989 | Munro et al. |
| 4,685,469 A | 8/1987 | Keller et al. | | 4,834,731 A | 5/1989 | Nowak et al. |
| 4,685,903 A | 8/1987 | Cable et al. | | 4,838,857 A | 6/1989 | Strowe et al. |
| 4,686,987 A | 8/1987 | Salo et al. | | 4,840,068 A | 6/1989 | Mayhew, Jr. |
| 4,687,530 A | 8/1987 | Berscheid et al. | | 4,840,350 A | 6/1989 | Cook et al. |
| 4,689,979 A | 9/1987 | Otsuka et al. | | 4,844,002 A | 7/1989 | Yasui et al. |
| 4,691,694 A | 9/1987 | Boyd et al. | | 4,846,153 A | 7/1989 | Berci |
| 4,691,710 A | 9/1987 | Dickens et al. | | 4,846,191 A | 7/1989 | Brockway et al. |
| 4,693,253 A | 9/1987 | Adams | | 4,846,664 A | 7/1989 | Hehl et al. |
| 4,695,237 A | 9/1987 | Inaba et al. | | 4,854,328 A | 8/1989 | Pollack |
| 4,696,189 A | 9/1987 | Hochreuther et al. | | 4,863,470 A | 9/1989 | Carter |
| 4,697,574 A | 10/1987 | Karcher et al. | | 4,865,587 A | 9/1989 | Walling |
| 4,698,038 A | 10/1987 | Key et al. | | 4,867,160 A | 9/1989 | Schaldach et al. |
| 4,700,497 A | 10/1987 | Sato et al. | | 4,867,498 A | 9/1989 | Delphia et al. |
| 4,700,610 A | 10/1987 | Bauer et al. | | 4,867,618 A | 9/1989 | Brohammer |
| 4,701,143 A | 10/1987 | Key et al. | | 4,869,252 A | 9/1989 | Gilli |
| 4,703,756 A | 11/1987 | Gough et al. | | 4,870,258 A | 9/1989 | Mochizuki et al. |
| 4,705,507 A | 11/1987 | Boyles | | 4,871,351 A | 10/1989 | Feingold et al. |
| 4,706,948 A | 11/1987 | Kroecher et al. | | 4,872,483 A | 10/1989 | Shah |
| 4,712,562 A | 12/1987 | Ohayon et al. | | 4,872,869 A | 10/1989 | Johns |
| 4,718,425 A | 1/1988 | Tanaka et al. | | 4,873,677 A | 10/1989 | Sakamoto et al. |
| 4,722,348 A | 2/1988 | Ligtenberg et al. | | 4,875,483 A | 10/1989 | Vollmann et al. |
| 4,724,806 A | 2/1988 | Hartwig et al. | | 4,880,004 A | 11/1989 | Baker, Jr. et al. |
| 4,724,830 A | 2/1988 | Fischell | | 4,882,678 A | 11/1989 | Hollis et al. |
| 4,725,826 A | 2/1988 | Hunter | | 4,886,392 A | 12/1989 | Iio et al. |
| 4,728,479 A | 3/1988 | Merkovsky | | 4,895,151 A | 1/1990 | Grevis et al. |
| 4,729,517 A | 3/1988 | Krokor et al. | | 4,896,594 A | 1/1990 | Baur et al. |
| 4,730,188 A | 3/1988 | Milheiser | | 4,898,158 A | 2/1990 | Daly et al. |
| 4,730,420 A | 3/1988 | Stratmann et al. | | 4,898,578 A | 2/1990 | Rubalcaba, Jr. |
| 4,730,619 A | 3/1988 | Koning et al. | | 4,899,751 A | 2/1990 | Cohen |
| 4,731,058 A | 3/1988 | Doan | | 4,899,752 A | 2/1990 | Cohen |
| 4,735,205 A | 4/1988 | Chachques et al. | | 4,902,277 A | 2/1990 | Mathies et al. |
| 4,738,267 A | 4/1988 | Lazorthes et al. | | 4,903,701 A | 2/1990 | Moore et al. |
| 4,738,268 A | 4/1988 | Kipnis | | 4,909,678 A | 3/1990 | Kakimoto et al. |
| 4,741,345 A | 5/1988 | Matthews et al. | | 4,913,147 A | 4/1990 | Fahlstrom et al. |
| 4,741,732 A | 5/1988 | Crankshaw et al. | | 4,919,143 A | 4/1990 | Ayers |
| 4,743,129 A | 5/1988 | Keryhuel et al. | | 4,924,872 A | 5/1990 | Frank |
| 4,745,541 A | 5/1988 | Vaniglia et al. | | 4,926,903 A | 5/1990 | Kawai et al. |
| 4,746,830 A | 5/1988 | Holland | | 4,932,406 A | 6/1990 | Berkovits |
| 4,750,495 A | 6/1988 | Moore et al. | | 4,934,369 A | 6/1990 | Maxwell |
| 4,752,115 A | 6/1988 | Murray, Jr. et al. | | 4,936,304 A | 6/1990 | Kresh et al. |
| 4,752,658 A | 6/1988 | Mack | | 4,940,037 A | 7/1990 | Eckert et al. |
| 4,757,463 A | 7/1988 | Ballou et al. | | 4,941,718 A | 7/1990 | Alexander, III et al. |
| 4,759,386 A | 7/1988 | Grouw, III | | 4,942,004 A | 7/1990 | Catanzaro |
| 4,763,649 A | 8/1988 | Merrick | | 4,944,050 A | 7/1990 | Shames et al. |
| 4,765,001 A | 8/1988 | Smith | | 4,944,298 A | 7/1990 | Sholder |
| 4,767,406 A | 8/1988 | Wadham et al. | | 4,944,307 A | 7/1990 | Hon et al. |
| 4,769,001 A | 9/1988 | Prince | | 4,945,761 A | 8/1990 | Lessi et al. |
| 4,772,896 A | 9/1988 | Nakatsu et al. | | 4,949,724 A | 8/1990 | Mahutte et al. |
| 4,773,401 A | 9/1988 | Citak et al. | | 4,952,205 A | 8/1990 | Mauerer et al. |
| 4,774,950 A | 10/1988 | Cohen | | 4,952,928 A | 8/1990 | Carroll et al. |
| 4,774,955 A | 10/1988 | Jones | | 4,953,563 A | 9/1990 | Kaiser et al. |
| 4,777,953 A | 10/1988 | Ash et al. | | 4,954,677 A | 9/1990 | Alberter et al. |
| 4,779,626 A | 10/1988 | Peel et al. | | 4,958,630 A | 9/1990 | Rosenbluth et al. |
| 4,781,192 A | 11/1988 | Demer | | 4,958,645 A | 9/1990 | Cadell et al. |
| 4,782,826 A | 11/1988 | Fogarty | | 4,960,424 A | 10/1990 | Grooters |
| 4,783,106 A | 11/1988 | Nutter | | 4,960,966 A | 10/1990 | Evans et al. |
| 4,788,847 A | 12/1988 | Sterghos | | 4,967,585 A | 11/1990 | Grimaldo |
| 4,791,318 A | 12/1988 | Lewis et al. | | 4,967,761 A | 11/1990 | Nathanielsz |
| 4,794,803 A | 1/1989 | Osterhout et al. | | 4,970,823 A | 11/1990 | Chen et al. |

| | | |
|---|---|---|
| 4,971,251 A | 11/1990 | Dobrick et al. |
| 4,977,896 A | 12/1990 | Robinson et al. |
| 4,978,335 A | 12/1990 | Arthur, III |
| 4,978,338 A | 12/1990 | Melsky et al. |
| 4,979,730 A | 12/1990 | Holbrook et al. |
| 4,980,671 A | 12/1990 | McCurdy |
| 4,981,141 A | 1/1991 | Segalowitz |
| 4,981,173 A | 1/1991 | Perkins et al. |
| 4,981,426 A | 1/1991 | Aoki et al. |
| 4,987,897 A | 1/1991 | Funke et al. |
| 4,988,337 A | 1/1991 | Ito et al. |
| 4,992,794 A | 2/1991 | Brouwers et al. |
| 4,997,556 A | 3/1991 | Yano et al. |
| 5,001,528 A | 3/1991 | Bahraman |
| 5,003,807 A | 4/1991 | Terrell et al. |
| 5,003,975 A | 4/1991 | Hafelfinger et al. |
| 5,003,976 A | 4/1991 | Alt et al. |
| 5,004,472 A | 4/1991 | Wallace |
| 5,004,873 A | 4/1991 | Schnut |
| 5,005,574 A | 4/1991 | Fearnot et al. |
| 5,005,586 A | 4/1991 | Lahr |
| 5,006,844 A | 4/1991 | Ohta et al. |
| 5,007,401 A | 4/1991 | Grohn et al. |
| 5,007,430 A | 4/1991 | Dardik |
| 5,007,919 A | 4/1991 | Silva et al. |
| 5,009,662 A | 4/1991 | Wallace et al. |
| 5,010,893 A | 4/1991 | Sholder |
| 5,012,286 A | 4/1991 | Kawano et al. |
| 5,012,810 A | 5/1991 | Strand et al. |
| 5,013,292 A | 5/1991 | Lemay et al. |
| 5,014,040 A | 5/1991 | Weaver et al. |
| 5,019,032 A | 5/1991 | Robertson |
| 5,019,041 A | 5/1991 | Robinson et al. |
| 5,020,845 A | 6/1991 | Falcoff et al. |
| 5,021,046 A | 6/1991 | Wallace |
| 5,022,395 A | 6/1991 | Russie |
| 5,024,965 A | 6/1991 | Chang et al. |
| 5,026,180 A | 6/1991 | Tajima et al. |
| 5,026,360 A | 6/1991 | Johnsen et al. |
| 5,028,918 A | 7/1991 | Giles et al. |
| 5,032,822 A | 7/1991 | Sweet |
| 5,036,869 A | 8/1991 | Inahara et al. |
| 5,038,800 A | 8/1991 | Oba et al. |
| 5,041,086 A | 8/1991 | Koenig et al. |
| 5,041,826 A | 8/1991 | Milheiser |
| 5,042,503 A | 8/1991 | Torok et al. |
| 5,044,770 A | 9/1991 | Haghkar |
| 5,046,661 A | 9/1991 | Kimura et al. |
| 5,048,060 A | 9/1991 | Arai et al. |
| 5,050,922 A | 9/1991 | Falcoff |
| 5,052,910 A | 10/1991 | Hehl et al. |
| 5,053,008 A | 10/1991 | Bajaj |
| 5,057,078 A | 10/1991 | Foote et al. |
| 5,058,583 A | 10/1991 | Geddes et al. |
| 5,061,239 A | 10/1991 | Shiels |
| 5,062,052 A | 10/1991 | Sparer et al. |
| 5,062,053 A | 10/1991 | Shirai et al. |
| 5,062,559 A | 11/1991 | Falcoff |
| 5,064,974 A | 11/1991 | Vigneau et al. |
| 5,067,960 A | 11/1991 | Grandjean et al. |
| 5,068,779 A | 11/1991 | Sullivan et al. |
| 5,069,680 A | 12/1991 | Grandjean |
| 5,077,102 A | 12/1991 | Chong |
| 5,077,870 A | 1/1992 | Melbye et al. |
| 5,078,139 A | 1/1992 | Strand et al. |
| 5,082,006 A | 1/1992 | Jonasson et al. |
| 5,083,563 A | 1/1992 | Collins et al. |
| 5,084,699 A | 1/1992 | DeMichele |
| 5,085,224 A | 2/1992 | Galen et al. |
| 5,085,258 A | 2/1992 | Fink, Jr. et al. |
| 5,089,673 A | 2/1992 | Strzodka et al. |
| 5,089,979 A | 2/1992 | McEachern et al. |
| 5,095,309 A | 3/1992 | Troyk et al. |
| 5,096,271 A | 3/1992 | Portman |
| 5,097,831 A | 3/1992 | Lekholm |
| 5,098,384 A | 3/1992 | Abrams |
| 5,103,832 A | 4/1992 | Jackson |
| 5,105,810 A | 4/1992 | Collins et al. |
| 5,107,850 A | 4/1992 | Olive |
| 5,112,344 A | 5/1992 | Petros et al. |
| 5,113,859 A | 5/1992 | Funke et al. |
| 5,113,869 A | 5/1992 | Nappholz et al. |
| 5,115,676 A | 5/1992 | Lee |
| 5,117,825 A | 6/1992 | Grevious |
| 5,121,777 A | 6/1992 | Leininger et al. |
| 5,127,451 A | 7/1992 | Fink, Jr. et al. |
| 5,129,394 A | 7/1992 | Mehra |
| 5,129,806 A | 7/1992 | Hehl et al. |
| 5,131,145 A | 7/1992 | Badoureaux et al. |
| 5,131,388 A | 7/1992 | Pless et al. |
| 5,133,358 A | 7/1992 | Gustafson et al. |
| 5,135,488 A | 8/1992 | Foote et al. |
| 5,139,484 A | 8/1992 | Hazon et al. |
| 5,144,949 A | 9/1992 | Olson |
| 5,148,580 A | 9/1992 | Dyckow et al. |
| 5,148,695 A | 9/1992 | Ellis |
| 5,152,770 A | 10/1992 | Bengmark et al. |
| 5,152,776 A | 10/1992 | Pinchuk |
| 5,154,170 A | 10/1992 | Bennett et al. |
| 5,154,171 A | 10/1992 | Chirife et al. |
| 5,154,693 A | 10/1992 | East et al. |
| 5,156,972 A | 10/1992 | Issachar et al. |
| 5,158,078 A | 10/1992 | Bennett et al. |
| 5,163,429 A | 11/1992 | Cohen |
| 5,167,615 A | 12/1992 | East et al. |
| 5,168,757 A | 12/1992 | Rabenau et al. |
| 5,168,982 A | 12/1992 | Hakanen et al. |
| 5,171,299 A | 12/1992 | Heitzmann et al. |
| 5,173,873 A | 12/1992 | Wu et al. |
| 5,174,286 A | 12/1992 | Chirife et al. |
| 5,174,291 A | 12/1992 | Schoonen et al. |
| 5,176,502 A | 1/1993 | Sanderson et al. |
| 5,178,197 A | 1/1993 | Healy |
| 5,181,423 A | 1/1993 | Philipps et al. |
| 5,181,517 A | 1/1993 | Hickey |
| 5,184,132 A | 2/1993 | Baird |
| 5,184,614 A | 2/1993 | Collins et al. |
| 5,184,619 A | 2/1993 | Austin |
| 5,185,535 A | 2/1993 | Farb et al. |
| 5,186,224 A | 2/1993 | Schirmacher et al. |
| 5,188,106 A | 2/1993 | Nappholz et al. |
| 5,188,604 A | 2/1993 | Orth |
| 5,192,314 A | 3/1993 | Daskalakis |
| 5,195,362 A | 3/1993 | Eason |
| 5,197,322 A | 3/1993 | Indravudh |
| 5,199,427 A | 4/1993 | Strickland |
| 5,199,428 A | 4/1993 | Obel et al. |
| 5,201,753 A | 4/1993 | Lampropoulos et al. |
| 5,204,670 A | 4/1993 | Stinton |
| 5,207,429 A | 5/1993 | Walmsley et al. |
| 5,209,223 A | 5/1993 | McGorry et al. |
| 5,209,732 A | 5/1993 | Lampropoulos et al. |
| 5,211,129 A | 5/1993 | Taylor et al. |
| 5,211,161 A | 5/1993 | Stef et al. |
| 5,212,476 A | 5/1993 | Maloney |
| 5,213,331 A | 5/1993 | Avanzini |
| 5,215,523 A | 6/1993 | Williams et al. |
| 5,218,343 A | 6/1993 | Stobbe et al. |
| 5,218,957 A | 6/1993 | Strickland |
| 5,226,429 A | 7/1993 | Kuzmak |
| 5,226,604 A | 7/1993 | Seiffert et al. |
| 5,230,694 A | 7/1993 | Rosenblum |
| 5,233,985 A | 8/1993 | Hudrlik |
| 5,235,326 A | 8/1993 | Beigel et al. |
| 5,244,269 A | 9/1993 | Harriehausen et al. |
| 5,244,461 A | 9/1993 | Derlien et al. |
| 5,246,008 A | 9/1993 | Mueller et al. |
| 5,249,858 A | 10/1993 | Nusser |
| 5,250,020 A | 10/1993 | Bley |
| 5,254,096 A | 10/1993 | Rondelet et al. |
| 5,256,157 A | 10/1993 | Samiotes et al. |
| 5,263,244 A | 11/1993 | Centa et al. |
| 5,263,981 A | 11/1993 | Polyak et al. |
| 5,267,940 A | 12/1993 | Moulder |
| 5,267,942 A | 12/1993 | Saperston |
| 5,269,891 A | 12/1993 | Colin et al. |
| 5,271,395 A | 12/1993 | Wahlstrand et al. |
| 5,274,859 A | 1/1994 | Redman et al. |

| | | | | | | |
|---|---|---|---|---|---|---|
| 5,280,789 A | 1/1994 | Potts | | 5,493,738 A | 2/1996 | Sanderson et al. |
| 5,282,839 A | 2/1994 | Roline et al. | | 5,494,036 A | 2/1996 | Uber, III et al. |
| 5,282,840 A | 2/1994 | Hudrlik | | 5,494,193 A | 2/1996 | Kirschner et al. |
| 5,291,894 A | 3/1994 | Nagy et al. | | 5,504,474 A | 4/1996 | Libman et al. |
| 5,292,219 A | 3/1994 | Merin et al. | | 5,505,916 A | 4/1996 | Berry, Jr. |
| 5,295,967 A | 3/1994 | Rondelet et al. | | 5,507,412 A | 4/1996 | Ebert et al. |
| 5,298,022 A | 3/1994 | Bernardi et al. | | 5,507,737 A | 4/1996 | Palmskog et al. |
| 5,298,884 A | 3/1994 | Gilmore et al. | | 5,507,785 A | 4/1996 | Deno |
| 5,300,093 A | 4/1994 | Koestner et al. | | 5,509,888 A | 4/1996 | Miller |
| 5,300,120 A | 4/1994 | Knapp et al. | | 5,509,891 A | 4/1996 | DeRidder |
| 5,304,112 A | 4/1994 | Mrklas et al. | | 5,513,945 A | 5/1996 | Hartmann et al. |
| 5,305,923 A | 4/1994 | Kirschner et al. | | 5,514,103 A | 5/1996 | Srisathapat et al. |
| 5,312,443 A | 5/1994 | Adams et al. | | 5,518,504 A | 5/1996 | Polyak |
| 5,312,452 A | 5/1994 | Salo | | 5,520,606 A | 5/1996 | Schoolman et al. |
| 5,312,453 A | 5/1994 | Shelton et al. | | 5,523,740 A | 6/1996 | Burgmann et al. |
| 5,313,953 A | 5/1994 | Yomtov et al. | | 5,534,018 A | 7/1996 | Wahlstrand et al. |
| 5,314,451 A | 5/1994 | Mulier | | 5,535,752 A | 7/1996 | Halperin et al. |
| 5,314,457 A | 5/1994 | Jeutter et al. | | 5,538,005 A | 7/1996 | Harrison et al. |
| 5,324,315 A | 6/1994 | Grevious | | 5,541,857 A | 7/1996 | Walter et al. |
| 5,325,834 A | 7/1994 | Ballheimer et al. | | 5,542,821 A * | 8/1996 | Dugan ............................ 417/53 |
| 5,326,249 A | 7/1994 | Weissfloch et al. | | 5,545,140 A | 8/1996 | Conero et al. |
| 5,328,460 A | 7/1994 | Lord et al. | | 5,545,151 A | 8/1996 | O'Connor et al. |
| 5,330,511 A | 7/1994 | Boute et al. | | 5,545,186 A | 8/1996 | Olson et al. |
| 5,337,750 A | 8/1994 | Walloch | | 5,545,214 A | 8/1996 | Stevens |
| 5,341,430 A | 8/1994 | Aulia et al. | | 5,547,470 A | 8/1996 | Johnson et al. |
| 5,342,401 A | 8/1994 | Spano et al. | | 5,551,427 A | 9/1996 | Altman |
| 5,342,406 A | 8/1994 | Thompson | | 5,551,439 A | 9/1996 | Hickey |
| 5,344,388 A | 9/1994 | Maxwell et al. | | 5,554,185 A | 9/1996 | Block et al. |
| 5,347,476 A | 9/1994 | McBean, Sr. | | 5,558,644 A | 9/1996 | Boyd et al. |
| 5,348,210 A | 9/1994 | Linzell et al. | | 5,564,434 A | 10/1996 | Halperin et al. |
| 5,348,536 A | 9/1994 | Young et al. | | 5,575,770 A | 11/1996 | Melsky et al. |
| 5,350,413 A | 9/1994 | Miller et al. | | 5,584,803 A | 12/1996 | Stevens et al. |
| 5,352,180 A | 10/1994 | Candelon et al. | | 5,586,629 A | 12/1996 | Shoberg et al. |
| 5,353,622 A | 10/1994 | Theener | | 5,593,430 A | 1/1997 | Renger |
| 5,353,800 A | 10/1994 | Pohndorf et al. | | 5,594,665 A | 1/1997 | Walter et al. |
| 5,354,200 A | 10/1994 | Klein et al. | | 5,596,986 A | 1/1997 | Goldfarb |
| 5,354,316 A | 10/1994 | Keimel | | 5,597,284 A | 1/1997 | Weltlich et al. |
| 5,354,319 A | 10/1994 | Wyborny et al. | | 5,610,083 A | 3/1997 | Chan et al. |
| 5,360,407 A | 11/1994 | Leonard et al. | | 5,611,768 A | 3/1997 | Tutrone, Jr. |
| 5,365,462 A | 11/1994 | McBean, Sr. | | 5,612,497 A | 3/1997 | Walter et al. |
| 5,365,619 A | 11/1994 | Solomon | | 5,615,671 A | 4/1997 | Schoonen et al. |
| 5,365,985 A | 11/1994 | Todd et al. | | 5,619,991 A | 4/1997 | Sloane |
| 5,368,040 A | 11/1994 | Carney | | 5,625,946 A | 5/1997 | Wildeson et al. |
| 5,370,665 A | 12/1994 | Hudrlik | | 5,626,623 A | 5/1997 | Kieval et al. |
| 5,373,852 A | 12/1994 | Harrison et al. | | 5,626,630 A | 5/1997 | Markowitz et al. |
| 5,375,073 A | 12/1994 | McBean | | 5,630,836 A | 5/1997 | Prem et al. |
| 5,377,128 A | 12/1994 | McBean | | 5,634,255 A | 6/1997 | Bishop et al. |
| 5,378,231 A | 1/1995 | Johnson et al. | | 5,637,083 A | 6/1997 | Bertrand et al. |
| 5,382,232 A | 1/1995 | Hague et al. | | 5,643,207 A | 7/1997 | Rise |
| 5,383,915 A | 1/1995 | Adams | | 5,645,116 A | 7/1997 | McDonald |
| 5,388,578 A | 2/1995 | Yomtov et al. | | 5,650,766 A | 7/1997 | Burgmann et al. |
| 5,388,586 A | 2/1995 | Lee et al. | | 5,673,585 A | 10/1997 | Bishop et al. |
| 5,388,831 A | 2/1995 | Quadri et al. | | 5,676,690 A | 10/1997 | Noren et al. |
| 5,394,909 A | 3/1995 | Mitchell et al. | | 5,681,285 A | 10/1997 | Ford et al. |
| 5,402,944 A | 4/1995 | Pape et al. | | 5,686,831 A | 11/1997 | Vandervalk et al. |
| 5,406,957 A | 4/1995 | Tansey | | 5,687,734 A | 11/1997 | Dempsey et al. |
| 5,409,009 A | 4/1995 | Olson | | 5,693,076 A | 12/1997 | Kaemmerer |
| 5,411,031 A | 5/1995 | Yomtov | | 5,702,368 A | 12/1997 | Stevens et al. |
| 5,411,551 A | 5/1995 | Winston et al. | | 5,702,427 A | 12/1997 | Ecker et al. |
| 5,411,552 A | 5/1995 | Andersen et al. | | 5,702,431 A | 12/1997 | Wang et al. |
| 5,416,372 A | 5/1995 | Ljungstroem et al. | | 5,704,352 A | 1/1998 | Tremblay et al. |
| 5,417,226 A | 5/1995 | Juma | | 5,715,786 A | 2/1998 | Seiberth et al. |
| 5,417,717 A | 5/1995 | Salo et al. | | 5,715,837 A | 2/1998 | Chen |
| 5,425,362 A | 6/1995 | Siker et al. | | 5,720,436 A | 2/1998 | Buschor et al. |
| 5,431,171 A | 7/1995 | Harrison et al. | | 5,730,101 A | 3/1998 | Aupperle et al. |
| 5,431,694 A | 7/1995 | Snaper et al. | | 5,732,710 A | 3/1998 | Rabinovich et al. |
| 5,433,694 A | 7/1995 | Lim et al. | | 5,733,313 A | 3/1998 | Barreras, Sr. et al. |
| 5,437,605 A | 8/1995 | Helmy et al. | | 5,738,652 A | 4/1998 | Boyd et al. |
| 5,443,215 A | 8/1995 | Fackler | | 5,742,233 A | 4/1998 | Hoffman et al. |
| 5,447,519 A | 9/1995 | Peterson | | 5,743,267 A | 4/1998 | Nikolic et al. |
| 5,449,368 A | 9/1995 | Kuzmak | | 5,749,369 A | 5/1998 | Rabinovich et al. |
| 5,456,690 A | 10/1995 | Duong-Van | | 5,749,909 A | 5/1998 | Schroeppel et al. |
| 5,461,390 A | 10/1995 | Hoshen | | 5,755,687 A | 5/1998 | Donlon |
| 5,464,435 A | 11/1995 | Neumann | | 5,755,748 A | 5/1998 | Borza et al. |
| 5,467,627 A | 11/1995 | Smith et al. | | 5,765,568 A | 6/1998 | Sweezer, Jr. et al. |
| 5,474,226 A | 12/1995 | Joseph | | 5,769,812 A | 6/1998 | Stevens et al. |
| 5,479,818 A | 1/1996 | Walter et al. | | 5,771,903 A | 6/1998 | Jakobsson |
| 5,482,049 A | 1/1996 | Addiss et al. | | 5,782,774 A | 7/1998 | Shmulewitz |
| 5,487,760 A | 1/1996 | Villafana | | 5,787,520 A | 8/1998 | Dunbar |

| | | | | | | |
|---|---|---|---|---|---|---|
| 5,791,344 | A | 8/1998 | Schulman et al. | 6,309,350 B1 | 10/2001 | VanTassel et al. |
| 5,792,094 | A | 8/1998 | Stevens et al. | 6,315,769 B1 | 11/2001 | Peer et al. |
| 5,792,179 | A | 8/1998 | Sideris | 6,319,208 B1 | 11/2001 | Abita et al. |
| 5,795,325 | A | 8/1998 | Valley et al. | 6,328,699 B1 | 12/2001 | Eigler et al. |
| 5,796,827 | A | 8/1998 | Coppersmith et al. | 6,338,735 B1 | 1/2002 | Stevens |
| 5,800,375 | A | 9/1998 | Sweezer et al. | 6,357,438 B1 | 3/2002 | Hansen |
| 5,807,265 | A | 9/1998 | Itoigawa et al. | 6,360,122 B1 | 3/2002 | Fischell et al. |
| 5,807,336 | A | 9/1998 | Russo et al. | 6,360,822 B1 | 3/2002 | Robertson et al. |
| 5,810,015 | A | 9/1998 | Flaherty | 6,366,817 B1 | 4/2002 | Kung |
| 5,810,757 | A | 9/1998 | Sweezer, Jr. et al. | 6,379,308 B1 | 4/2002 | Brockway et al. |
| 5,814,016 | A | 9/1998 | Valley et al. | 6,379,380 B1 | 4/2002 | Satz |
| 5,817,093 | A | 10/1998 | Williamson, IV et al. | 6,398,752 B1 | 6/2002 | Sweezer, Jr. et al. |
| 5,833,603 | A | 11/1998 | Kovacs et al. | 6,409,674 B1 | 6/2002 | Brockway et al. |
| 5,836,300 | A | 11/1998 | Mault | 6,423,031 B1 | 7/2002 | Donlon |
| 5,836,886 | A | 11/1998 | Itoigawa et al. | 6,430,444 B1 | 8/2002 | Borza et al. |
| 5,840,081 | A | 11/1998 | Andersen et al. | 6,431,175 B1 | 8/2002 | Penner et al. |
| 5,849,225 | A | 12/1998 | Ebina et al. | 6,432,040 B1 | 8/2002 | Meah |
| 5,855,597 | A | 1/1999 | Jayaraman et al. | 6,443,887 B1 | 9/2002 | Derus et al. |
| 5,855,601 | A | 1/1999 | Bessler et al. | 6,443,893 B1 | 9/2002 | Schnakenberg et al. |
| 5,860,938 | A | 1/1999 | Lafontaine et al. | 6,450,173 B1 | 9/2002 | Forsell et al. |
| 5,861,018 | A | 1/1999 | Feierbach | 6,450,946 B1 | 9/2002 | Forsell et al. |
| 5,863,366 | A | 1/1999 | Snow | 6,453,907 B1 | 9/2002 | Forsell et al. |
| 5,868,702 | A | 2/1999 | Stevens et al. | 6,454,698 B1 | 9/2002 | Forsell et al. |
| 5,873,837 | A | 2/1999 | Lieber et al. | 6,454,699 B1 | 9/2002 | Forsell et al. |
| 5,875,953 | A | 3/1999 | Shioya et al. | 6,454,700 B1 | 9/2002 | Forsell et al. |
| 5,879,499 | A | 3/1999 | Corvi | 6,454,701 B1 | 9/2002 | Forsell et al. |
| 5,881,919 | A | 3/1999 | Womac et al. | 6,461,292 B1 | 10/2002 | Forsell et al. |
| 5,885,238 | A | 3/1999 | Stevens et al. | 6,461,293 B1 | 10/2002 | Forsell et al. |
| 5,887,475 | A | 3/1999 | Muldner | 6,463,329 B1 | 10/2002 | Goedeke |
| 5,899,927 | A | 5/1999 | Ecker et al. | 6,463,935 B1 | 10/2002 | Forsell et al. |
| 5,916,179 | A | 6/1999 | Sharrock | 6,464,628 B1 | 10/2002 | Forsell et al. |
| 5,916,237 | A | 6/1999 | Schu | 6,470,212 B1 | 10/2002 | Weijand et al. |
| 5,935,078 | A | 8/1999 | Feierbach | 6,470,892 B1 | 10/2002 | Forsell et al. |
| 5,938,669 | A | 8/1999 | Klaiber et al. | 6,471,635 B1 | 10/2002 | Forsell et al. |
| 5,951,487 | A | 9/1999 | Brehmeier-Flick et al. | 6,475,136 B1 | 11/2002 | Forsell et al. |
| 5,957,861 | A | 9/1999 | Combs et al. | 6,475,170 B1 | 11/2002 | Doron et al. |
| 5,967,986 | A | 10/1999 | Cimochowski et al. | 6,482,145 B1 | 11/2002 | Forsell et al. |
| 5,971,934 | A | 10/1999 | Scherer et al. | 6,482,171 B1 | 11/2002 | Corvi et al. |
| 5,974,873 | A | 11/1999 | Nelson et al. | 6,482,177 B1 | 11/2002 | Leinders et al. |
| 5,978,985 | A | 11/1999 | Thurman | 6,486,588 B2 | 11/2002 | Doron et al. |
| 5,995,874 | A | 11/1999 | Borza et al. | 6,503,189 B1 | 1/2003 | Forsell et al. |
| 6,015,386 | A | 1/2000 | Kensey et al. | 6,504,286 B1 | 1/2003 | Porat et al. |
| 6,015,387 | A | 1/2000 | Schwartz et al. | 6,531,739 B2 | 3/2003 | Cable et al. |
| 6,019,729 | A | 2/2000 | Itoigawa et al. | 6,533,719 B2 | 3/2003 | Kuyava et al. |
| 6,024,704 | A | 2/2000 | Meador et al. | 6,533,733 B1 | 3/2003 | Ericson et al. |
| 6,030,413 | A | 2/2000 | Lazarus | 6,542,350 B1 | 4/2003 | Rogers |
| 6,033,366 | A | 3/2000 | Brockway et al. | 6,558,321 B1 | 5/2003 | Burd et al. |
| 6,035,461 | A | 3/2000 | Nguyen | 6,558,994 B2 | 5/2003 | Cha et al. |
| 6,053,873 | A | 4/2000 | Govari et al. | 6,573,563 B2 | 6/2003 | Lee et al. |
| 6,056,723 | A | 5/2000 | Donlon | 6,582,462 B1 | 6/2003 | Andersen et al. |
| 6,058,330 | A | 5/2000 | Borza et al. | 6,599,250 B2 | 7/2003 | Webb et al. |
| 6,059,757 | A | 5/2000 | Macoviak et al. | 6,605,112 B1 | 8/2003 | Moll et al. |
| 6,067,474 | A | 5/2000 | Schulman et al. | 6,629,534 B1 | 10/2003 | St. Goar et al. |
| 6,067,991 | A | 5/2000 | Forsell et al. | 6,640,137 B2 | 10/2003 | MacDonald |
| 6,076,016 | A | 6/2000 | Feierbach | 6,641,610 B2 | 11/2003 | Wolf et al. |
| 6,083,174 | A | 7/2000 | Brehmeier-Flick et al. | 6,645,143 B2 | 11/2003 | VanTassel et al. |
| 6,090,096 | A | 7/2000 | St. Goar et al. | 6,673,109 B2 | 1/2004 | Cox |
| 6,102,678 | A | 8/2000 | Peclat et al. | 6,678,561 B2 | 1/2004 | Forsell et al. |
| 6,102,856 | A | 8/2000 | Groff et al. | 6,682,480 B1 | 1/2004 | Habib et al. |
| 6,102,922 | A | 8/2000 | Jakobsson et al. | 6,682,503 B1 | 1/2004 | Fariss et al. |
| 6,106,477 | A | 8/2000 | Miesel et al. | 6,682,559 B2 | 1/2004 | Myers et al. |
| 6,106,551 | A | 8/2000 | Crossett et al. | 6,695,866 B1 | 2/2004 | Kuehn et al. |
| 6,110,145 | A | 8/2000 | Macoviak | 6,709,385 B2 | 3/2004 | Forsell et al. |
| 6,113,553 | A | 9/2000 | Chubbuck | 6,718,200 B2 | 4/2004 | Marmaropoulos et al. |
| 6,131,664 | A | 10/2000 | Sonnier | 6,719,787 B2 | 4/2004 | Cox |
| 6,135,945 | A | 10/2000 | Sultan | 6,719,788 B2 | 4/2004 | Cox |
| 6,159,156 | A | 12/2000 | Van Bockel et al. | 6,719,789 B2 | 4/2004 | Cox |
| 6,162,180 | A | 12/2000 | Miesel et al. | 6,731,976 B2 | 5/2004 | Penn et al. |
| 6,162,245 | A | 12/2000 | Jayaraman et al. | 6,733,525 B2 | 5/2004 | Pease et al. |
| 6,168,614 | B1 | 1/2001 | Andersen et al. | 6,736,846 B2 | 5/2004 | Cox |
| 6,234,745 | B1 | 5/2001 | Pugh et al. | 6,752,813 B2 | 6/2004 | Goldfarb et al. |
| 6,240,316 | B1 | 5/2001 | Richmond et al. | 6,796,942 B1 | 9/2004 | Kreiner et al. |
| 6,240,318 | B1 | 5/2001 | Phillips | 6,822,343 B2 | 11/2004 | Estevez |
| 6,245,102 | B1 | 6/2001 | Jayaraman | 6,851,628 B1 | 2/2005 | Garrison et al. |
| 6,248,080 | B1 | 6/2001 | Miesel et al. | 6,855,115 B2 | 2/2005 | Fonseca et al. |
| 6,251,093 | B1 | 6/2001 | Valley et al. | 6,889,772 B2 | 5/2005 | Buytaert et al. |
| 6,269,819 | B1 | 8/2001 | Oz et al. | 6,890,300 B2 | 5/2005 | Lloyd et al. |
| 6,277,078 | B1 | 8/2001 | Porat et al. | 6,896,651 B2 | 5/2005 | Gross et al. |
| 6,292,697 | B1 | 9/2001 | Roberts | 6,896,690 B1 | 5/2005 | Lambrecht et al. |

| | | | | | | |
|---|---|---|---|---|---|---|
| 6,913,600 | B2 | 7/2005 | Valley et al. | 2005/0192642 A1 | 9/2005 | Forsell |
| 6,915,165 | B2 | 7/2005 | Forsell et al. | 2005/0240155 A1 | 10/2005 | Conlon |
| 6,926,246 | B2 | 8/2005 | Ginggen et al. | 2005/0240156 A1 | 10/2005 | Conlon |
| 6,929,653 | B2 | 8/2005 | Strecter | 2005/0250979 A1 | 11/2005 | Coe |
| 6,932,792 | B1 | 8/2005 | St. Goar et al. | 2005/0267406 A1 | 12/2005 | Hassler |
| 6,951,229 | B2 | 10/2005 | Garrison et al. | 2005/0267500 A1 | 12/2005 | Hassler et al. |
| 6,951,571 | B1 | 10/2005 | Srivastava | 2005/0272968 A1 | 12/2005 | Byrum et al. |
| 6,953,429 | B2 | 10/2005 | Forsell et al. | 2005/0277960 A1 | 12/2005 | Hassler et al. |
| 6,961,619 | B2 | 11/2005 | Casey | 2005/0277974 A1 | 12/2005 | Hassler et al. |
| 6,970,742 | B2 | 11/2005 | Mann et al. | 2005/0288604 A1 | 12/2005 | Eigler et al. |
| 6,979,350 | B2 | 12/2005 | Moll et al. | 2005/0288720 A1 | 12/2005 | Ross et al. |
| 6,985,078 | B2 | 1/2006 | Suzuki et al. | 2005/0288721 A1 | 12/2005 | Girouard et al. |
| 6,989,027 | B2 | 1/2006 | Allen et al. | 2005/0288739 A1 | 12/2005 | Hassler et al. |
| 7,011,095 | B2 | 3/2006 | Wolf et al. | 2005/0288740 A1 | 12/2005 | Hassler et al. |
| 7,011,624 | B2 | 3/2006 | Forsell et al. | 2005/0288741 A1 | 12/2005 | Hassler et al. |
| 7,017,583 | B2 | 3/2006 | Forsell et al. | 2005/0288742 A1 | 12/2005 | Giordano et al. |
| 7,018,406 | B2 | 3/2006 | Seguin et al. | 2006/0002035 A1 | 1/2006 | Gao et al. |
| 7,021,402 | B2 | 4/2006 | Beato et al. | 2006/0010090 A1 | 1/2006 | Brockway et al. |
| 7,025,727 | B2 | 4/2006 | Brockway et al. | 2006/0020224 A1 | 1/2006 | Geiger |
| 7,044,920 | B2 | 5/2006 | Letort et al. | 2006/0020305 A1 | 1/2006 | Desai et al. |
| 7,060,080 | B2 | 6/2006 | Bachmann et al. | 2006/0035446 A1 | 2/2006 | Chang et al. |
| 7,081,683 | B2 | 7/2006 | Ariav et al. | 2006/0047205 A1 | 3/2006 | Ludomirsky et al. |
| 7,109,933 | B2 | 9/2006 | Ito et al. | 2006/0049714 A1 | 3/2006 | Liu et al. |
| 7,131,447 | B2 | 11/2006 | Sterman et al. | 2006/0058627 A1 | 3/2006 | Flaherty et al. |
| 7,131,945 | B2 | 11/2006 | Fink et al. | 2006/0064134 A1 | 3/2006 | Mazar et al. |
| 7,134,580 | B2 | 11/2006 | Garrison et al. | 2006/0085051 A1 | 4/2006 | Fritsch |
| 7,144,400 | B2 | 12/2006 | Byrum et al. | 2006/0089571 A1 | 4/2006 | Gertner |
| 7,147,640 | B2 | 12/2006 | Huebner et al. | 2006/0094966 A1 | 5/2006 | Brockway et al. |
| 7,153,262 | B2 | 12/2006 | Stivoric et al. | 2006/0100531 A1 | 5/2006 | Moser |
| 7,187,978 | B2 | 3/2007 | Malek et al. | 2006/0113187 A1 | 6/2006 | Deng et al. |
| 7,225,032 | B2 | 5/2007 | Schmeling et al. | 2006/0122285 A1 | 6/2006 | Falloon et al. |
| 7,257,438 | B2 | 8/2007 | Kinast | 2006/0122863 A1 | 6/2006 | Gottesman et al. |
| 7,285,090 | B2 | 10/2007 | Stivoric et al. | 2006/0142635 A1 | 6/2006 | Forsell |
| 2001/0011543 | A1 | 8/2001 | Forsell | 2006/0149124 A1 | 7/2006 | Forsell |
| 2001/0041823 | A1 | 11/2001 | Snyder et al. | 2006/0149324 A1 | 7/2006 | Mann et al. |
| 2002/0049394 | A1 | 4/2002 | Roy et al. | 2006/0149327 A1 | 7/2006 | Hedberg et al. |
| 2002/0120200 | A1 | 8/2002 | Brockway et al. | 2006/0157701 A1 | 7/2006 | Bauer et al. |
| 2002/0138009 | A1 | 9/2002 | Brockway et al. | 2006/0161186 A1 | 7/2006 | Hassler et al. |
| 2002/0177782 | A1 | 11/2002 | Penner | 2006/0178617 A1 | 8/2006 | Adams et al. |
| 2003/0009201 | A1 | 1/2003 | Forsell | 2006/0178695 A1 | 8/2006 | Decant et al. |
| 2003/0030893 | A1 | 2/2003 | Cornelius et al. | 2006/0183967 A1 | 8/2006 | Lechner |
| 2003/0032857 | A1 | 2/2003 | Forsell | 2006/0184206 A1 | 8/2006 | Baker et al. |
| 2003/0037591 | A1 | 2/2003 | Ashton et al. | 2006/0189887 A1 * | 8/2006 | Hassler et al. .............. 600/561 |
| 2003/0045775 | A1 | 3/2003 | Forsell | 2006/0189888 A1 | 8/2006 | Hassler et al. |
| 2003/0066536 | A1 | 4/2003 | Forsell | 2006/0189889 A1 | 8/2006 | Gertner |
| 2003/0088148 | A1 | 5/2003 | Forsell | 2006/0199997 A1 | 9/2006 | Hassler et al. |
| 2003/0092962 | A1 | 5/2003 | Forsell | 2006/0211912 A1 | 9/2006 | Dlugos et al. |
| 2003/0093117 | A1 | 5/2003 | Saadat | 2006/0211913 A1 | 9/2006 | Dlugos et al. |
| 2003/0100929 | A1 | 5/2003 | Forsell | 2006/0211914 A1 | 9/2006 | Hassler et al. |
| 2003/0105385 | A1 | 6/2003 | Forsell | 2006/0217668 A1 | 9/2006 | Schulze et al. |
| 2003/0109771 | A1 | 6/2003 | Forsell | 2006/0217673 A1 | 9/2006 | Schulze et al. |
| 2003/0114729 | A1 | 6/2003 | Forsell | 2006/0235310 A1 | 10/2006 | O'Brien et al. |
| 2003/0125605 | A1 | 7/2003 | Forsell | 2006/0235439 A1 | 10/2006 | Molitor et al. |
| 2003/0125768 | A1 | 7/2003 | Peter | 2006/0235448 A1 | 10/2006 | Roslin et al. |
| 2003/0135089 | A1 | 7/2003 | Forsell | 2006/0244914 A1 | 11/2006 | Cech et al. |
| 2003/0135090 | A1 | 7/2003 | Forsell | 2006/0247682 A1 | 11/2006 | Gerber et al. |
| 2003/0136417 | A1 | 7/2003 | Fonseca et al. | 2006/0247719 A1 | 11/2006 | Maschino et al. |
| 2003/0144648 | A1 | 7/2003 | Forsell | 2006/0247721 A1 | 11/2006 | Maschino et al. |
| 2003/0163079 | A1 | 8/2003 | Burnett | 2006/0247722 A1 | 11/2006 | Maschino et al. |
| 2003/0216666 | A1 | 11/2003 | Ericson et al. | 2006/0247723 A1 | 11/2006 | Gerber et al. |
| 2004/0054352 | A1 | 3/2004 | Adams et al. | 2006/0247724 A1 | 11/2006 | Gerber et al. |
| 2004/0113790 | A1 | 6/2004 | Hamel et al. | 2006/0247725 A1 | 11/2006 | Gerber et al. |
| 2004/0133092 | A1 | 7/2004 | Kain | 2006/0252982 A1 | 11/2006 | Hassler et al. |
| 2004/0147969 | A1 | 7/2004 | Mann et al. | 2006/0293625 A1 | 12/2006 | Hunt et al. |
| 2004/0172087 | A1 | 9/2004 | Forsell | 2006/0293626 A1 | 12/2006 | Byrum et al. |
| 2004/0186396 | A1 | 9/2004 | Roy et al. | 2006/0293627 A1 | 12/2006 | Byrum et al. |
| 2004/0254537 | A1 | 12/2004 | Conlon et al. | 2007/0010790 A1 | 1/2007 | Byrum et al. |
| 2005/0015014 | A1 | 1/2005 | Fonseca et al. | 2007/0025868 A1 * | 2/2007 | Swayze et al. .............. 417/474 |
| 2005/0025979 | A1 | 2/2005 | Sandt et al. | 2007/0027356 A1 | 2/2007 | Ortiz |
| 2005/0027175 | A1 | 2/2005 | Yang | 2007/0027493 A1 | 2/2007 | Ben-Haim et al. |
| 2005/0038328 | A1 | 2/2005 | Stoehrer et al. | 2007/0067206 A1 | 3/2007 | Haggerty et al. |
| 2005/0061079 | A1 | 3/2005 | Schulman | 2007/0070906 A1 | 3/2007 | Thakur |
| 2005/0102026 | A1 | 5/2005 | Turner et al. | 2007/0072452 A1 | 3/2007 | Inagaki et al. |
| 2005/0159789 | A1 | 7/2005 | Brockway et al. | 2007/0081304 A1 | 4/2007 | Takeguchi |
| 2005/0165317 | A1 | 7/2005 | Turner et al. | 2007/0156013 A1 | 7/2007 | Birk |
| 2005/0182330 | A1 | 8/2005 | Brockway et al. | 2007/0161958 A1 | 7/2007 | Glenn |
| 2005/0187482 | A1 | 8/2005 | O'Brien et al. | 2007/0167672 A1 | 7/2007 | Dlugos et al. |
| 2005/0187488 | A1 | 8/2005 | Wolf | 2007/0173881 A1 | 7/2007 | Birk et al. |
| 2005/0192531 | A1 * | 9/2005 | Birk .............. 604/96.01 | 2007/0179583 A1 | 8/2007 | Goetzinger et al. |

| | | | | | | |
|---|---|---|---|---|---|---|
| 2007/0208313 | A1 | 9/2007 | Conlon et al. | FR | 2730158 A1 | 8/1996 |
| 2007/0225781 | A1 | 9/2007 | Saadat et al. | GB | 2355937 | 5/2001 |
| 2007/0265645 | A1* | 11/2007 | Birk et al. .................. 606/157 | WO | WO-8911244 | 11/1989 |
| 2008/0009680 | A1 | 1/2008 | Hassler | WO | WO-8911701 | 11/1989 |
| 2008/0249806 | A1 | 10/2008 | Dlugos et al. | WO | WO-9004368 | 5/1990 |
| 2008/0250341 | A1 | 10/2008 | Dlugos et al. | WO | WO-9511057 | 4/1995 |
| 2009/0222065 | A1 | 9/2009 | Dlugos, Jr. et al. | WO | WO-9715351 | 5/1997 |

FOREIGN PATENT DOCUMENTS

| | | | | | |
|---|---|---|---|---|---|
| CA | 1119469 | 3/1982 | WO | WO-9733513 | 9/1997 |
| CA | 1275135 | 10/1990 | WO | WO-9833554 | 8/1998 |
| CA | 1277885 | 12/1990 | WO | WO-9835610 | 8/1998 |
| CA | 1317482 | 5/1993 | WO | WO-9901063 | 1/1999 |
| CA | 2082015 | 5/1993 | WO | WO-9918850 | 4/1999 |
| CA | 1327191 | 2/1994 | WO | 0009047 A1 | 2/2000 |
| CA | 2119101 | 9/1994 | WO | WO-0004945 | 2/2000 |
| CA | 2305998 | 4/1999 | WO | WO-0033738 | 6/2000 |
| CN | 1059035 | 2/1992 | WO | WO-0072899 | 12/2000 |
| CN | 1119469 | 3/1996 | WO | WO-0104487 | 1/2001 |
| CN | 1241003 | 1/2000 | WO | 0108597 A1 | 2/2001 |
| EA | 4581 | 6/2004 | WO | WO-0112075 | 2/2001 |
| EP | 125387 B1 | 11/1984 | WO | WO-0112076 | 2/2001 |
| EP | 417171 | 3/1991 | WO | WO-0112077 | 2/2001 |
| EP | 508141 | 10/1992 | WO | WO-0112078 | 2/2001 |
| EP | 568730 | 11/1993 | WO | WO-0121066 | 3/2001 |
| EP | 605302 | 7/1994 | WO | WO-0136014 | 5/2001 |
| EP | 660482 | 6/1995 | WO | WO-0145485 | 6/2001 |
| EP | 714017 | 5/1996 | WO | WO-0145486 | 6/2001 |
| EP | 769340 | 4/1997 | WO | WO-0147431 | 7/2001 |
| EP | 846475 | 6/1998 | WO | WO-0147432 | 7/2001 |
| EP | 848780 | 6/1998 | WO | WO-0147433 | 7/2001 |
| EP | 876808 | 11/1998 | WO | WO-0147434 | 7/2001 |
| EP | 888079 | 1/1999 | WO | WO-0147435 | 7/2001 |
| EP | 914059 | 5/1999 | WO | WO-0147440 | 7/2001 |
| EP | 0941712 A1 | 9/1999 | WO | WO-0147575 | 7/2001 |
| EP | 981293 | 3/2000 | WO | WO-0148451 | 7/2001 |
| EP | 997680 | 5/2000 | WO | WO-0149245 | 7/2001 |
| EP | 1003021 | 5/2000 | WO | WO-0150832 | 7/2001 |
| EP | 1022983 | 8/2000 | WO | WO-0150833 | 7/2001 |
| EP | 1050265 | 11/2000 | WO | WO-0154626 | 8/2001 |
| EP | 1115329 | 7/2001 | WO | WO-0158388 | 8/2001 |
| EP | 1119314 | 8/2001 | WO | WO-0158390 | 8/2001 |
| EP | 1128871 | 9/2001 | WO | WO-0158391 | 8/2001 |
| EP | 1202674 | 5/2002 | WO | WO-0158393 | 8/2001 |
| EP | 1213991 | 6/2002 | WO | WO-0160453 | 8/2001 |
| EP | 1253877 | 11/2002 | WO | WO-0181890 | 11/2001 |
| EP | 1253879 | 11/2002 | WO | WO-0200118 | 1/2002 |
| EP | 1253880 | 11/2002 | WO | WO-0215769 | 2/2002 |
| EP | 1253881 | 11/2002 | WO | WO-0226161 | 4/2002 |
| EP | 1253883 | 11/2002 | WO | WO-02053228 | 7/2002 |
| EP | 1253888 | 11/2002 | WO | WO-02055126 | 7/2002 |
| EP | 1255511 | 11/2002 | WO | WO-02058551 | 8/2002 |
| EP | 1255513 | 11/2002 | WO | WO-02065894 | 8/2002 |
| EP | 1255514 | 11/2002 | WO | WO-02076289 | 10/2002 |
| EP | 1263355 | 12/2002 | WO | WO-02082984 | 10/2002 |
| EP | 1263357 | 12/2002 | WO | WO-02089655 | 11/2002 |
| EP | 1284691 | 2/2003 | WO | WO-02090894 | 11/2002 |
| EP | 1374758 | 1/2004 | WO | WO-02100481 | 12/2002 |
| EP | 1488735 | 12/2004 | WO | WO-03002192 | 1/2003 |
| EP | 1500411 | 1/2005 | WO | WO-03002193 | 1/2003 |
| EP | 1510306 | 3/2005 | WO | WO-03020182 | 3/2003 |
| EP | 1518514 | 3/2005 | WO | WO-03061467 | 7/2003 |
| EP | 1545303 | 6/2005 | WO | WO-03061504 | 7/2003 |
| EP | 1547549 | 6/2005 | WO | WO-03096889 | 11/2003 |
| EP | 1563814 | 8/2005 | WO | 2004014245 A1 | 2/2004 |
| EP | 1568338 | 8/2005 | WO | WO-2004014456 | 2/2004 |
| EP | 1582175 | 10/2005 | WO | WO-2004019773 | 3/2004 |
| EP | 1582176 | 10/2005 | WO | WO-2004058101 | 7/2004 |
| EP | 1584303 | 10/2005 | WO | WO-2004066879 | 8/2004 |
| EP | 1586283 | 10/2005 | WO | WO-2004110263 | 12/2004 |
| EP | 1591086 | 11/2005 | WO | WO-2005000206 | 1/2005 |
| EP | 1593359 | 11/2005 | WO | WO-2005007075 | 1/2005 |
| EP | 1598030 | 11/2005 | WO | WO-2005107583 | 11/2005 |
| EP | 1609440 | 12/2005 | WO | WO-2006001851 | 1/2006 |
| EP | 1674033 | 6/2006 | WO | WO-2006035446 | 4/2006 |
| EP | 1736123 | 12/2006 | WO | 2006108203 A2 | 10/2006 |
| EP | 1799119 | 6/2007 | WO | WO-2006113187 | 10/2006 |
| EP | 1815881 A1 | 8/2007 | WO | 2006118790 A2 | 11/2006 |
| EP | 1832252 A2 | 9/2007 | WO | WO-2006122285 | 11/2006 |
| | | | WO | WO-2007067206 | 6/2007 |
| | | | WO | WO-2007070906 | 6/2007 |

| WO | WO-2007072452 | 6/2007 |
| WO | WO-2007081304 | 7/2007 |
| WO | WO-2007104356 | 9/2007 |

OTHER PUBLICATIONS

"Rad Hard Aerospace Components Products", Honeywell product and service information from website http://www.honeywell.com/sites/portal?smap=aerospace&page=Radiation-Hardened-Electronics3&theme=T6&catID=C815147E4-8786-29FE-49EB-C21C8790AA99&id=H0166BA51-5344-E57E-5C37-C6333EA43F61&sel=1; 1 page.

"Radiation Hardened Electronics and Radiation Technology", Honeywell product and service information from website http://www.honeywell.com/sites/portal?smap=aerospace&page=Radiation-Hardened-Electronics&theme=T4; 2 pages.

Kirchner, G., "Honeywell and Synopsys: Concept-to-Parts Solutions for Next Generation Rad-Hard ASICs", in online magazine Compiler, http://www.synopsys.com/news/pubs/compiler/artlead_redasic-apr05.html, Apr. 2005, 5 pages.

P.A. Neukomm and H. Kundig, "Passive Wireless Actuator Control and Sensor Signal Transmission," Sensors and Actuators, A21-A23 (1990) 258-262.

European Search Report, Application No. 08253986.7, Issued Mar. 30, 2009, 5 pages.

European Search Report, Application No. 09250497.6, Issued May 13, 2009, 11 pages.

\* cited by examiner

AUTOMATICALLY ADJUSTING BAND SYSTEM WITH MEMS PUMP

FIELD OF THE INVENTION

The present invention relates to implantable medical devices, and in particular implantable gastric restriction devices.

BACKGROUND OF THE INVENTION

Obesity is becoming a growing concern, particularly in the United States, as the number of obese people continues to increase, and more is learned about the negative health effects of obesity. Morbid obesity, in which a person is 100 pounds or more over ideal body weight, in particular poses significant risks for severe health problems. Accordingly, a great deal of attention is being focused on treating obese patients. One method of treating morbid obesity has been to place a restriction device, such as an elongated band, about the upper portion of the stomach. Gastric bands have typically comprised a fluid-filled elastomeric balloon with fixed endpoints that encircles the stomach just inferior to the esophageal-gastric junction to form a small gastric pouch above the band and a reduced stoma opening in the stomach. When fluid is infused into the balloon, the band expands against the stomach creating a food intake restriction or stoma in the stomach. To decrease this restriction, fluid is removed from the band. The effect of the band is to reduce the available stomach volume and thus the amount of food that can be consumed before becoming "full."

Food restriction devices have also comprised mechanically adjusted bands that similarly encircle the upper portion of the stomach. These bands include any number of resilient materials or gearing devices, as well as drive members, for adjusting the bands. Additionally, gastric bands have been developed that include both hydraulic and mechanical drive elements. An example of such an adjustable gastric band is disclosed in U.S. Pat. No. 6,067,991, entitled "Mechanical Food Intake Restriction Device" which issued on May 30, 2000, and is incorporated herein by reference. It is also known to restrict the available food volume in the stomach cavity by implanting an inflatable elastomeric balloon within the stomach cavity itself. The balloon is filled with a fluid to expand against the stomach walls and, thereby, decrease the available food volume within the stomach.

With each of the above-described food restriction devices, safe, effective treatment requires that the device be regularly monitored and adjusted to vary the degree of restriction applied to the stomach. With banding devices, the gastric pouch above the band will substantially increase in size following the initial implantation. Accordingly, the stoma opening in the stomach must initially be made large enough to enable the patient to receive adequate nutrition while the stomach adapts to the banding device. As the gastric pouch increases in size, the band may be adjusted to vary the stoma size. In addition, it is desirable to vary the stoma size in order to accommodate changes in the patient's body or treatment regime, or in a more urgent case, to relieve an obstruction or severe esophageal dilatation. Traditionally, adjusting a hydraulic gastric band required a scheduled clinician visit during which a Huber needle and syringe were used to penetrate the patient's skin and add or remove fluid from the balloon via an injection port. More recently, implantable pumps have been developed which enable non-invasive adjustments of the band. An external programmer communicates with the implanted pump using telemetry to control the pump. During a scheduled visit, a physician places a handheld portion of the programmer near the gastric implant and transmits power and command signals to the implant. The implant in turn adjusts the fluid levels in the band and transmits a response command to the programmer.

During these gastric band adjustments, it has been difficult to determine how the adjustment is proceeding, and whether the adjustment will have the intended effect. In an attempt to determine the efficacy of an adjustment, some physicians have utilized fluoroscopy with a Barium swallow as the adjustment is being performed. However, fluoroscopy is both expensive and undesirable due to the radiation doses incurred by both the physician and patient. Other physicians have instructed the patient to drink a glass of water during or after the adjustment to determine whether the water can pass through the adjusted stoma. This method, however, only assures that the patient is not obstructing, and does not provide any information about the efficacy of the adjustment. Oftentimes, a physician may simply adopt a "try as you go" method based upon their prior experience, and the results of an adjustment may not be discovered until hours or days later, when the patient experiences a complete obstruction to the stomach cavity, or the band induces erosion of the stomach tissue due to excessive interface pressures against the band.

Furthermore, the implantable pumps known in the art, such as centrifugal or positive displacement pumps, have high power requirements during operation. The power requirements of such pumps limit their usage for frequent adjustments to fluid levels in the band. Current pumps also require large housings to encase the mechanical pumping mechanism, gears, and motors, further limiting their usefulness as implantable pumps. Additional components, such as valves, are also necessary to maintain fluid pressure in the band when power is not supplied to conventional pumps. An example of an implantable pump system is described in US Patent Publication No. 2005/0277974, entitled "Thermodynamically driven reversible infuser pump for use as a remotely controlled gastric band" which was filed on May 28, 2004.

Accordingly, methods and devices are provided for use with a gastric restriction device, and in particular methods and devices are provided which allow adjustment of a gastric restriction device.

SUMMARY OF THE INVENTION

The present invention generally provides systems and methods for forming a restriction in a patient. In one exemplary embodiment, a restriction system includes an implantable restriction device and an implantable micro-electro-mechanical systems (MEMS) pump in fluid communication with the restriction device. Optionally, an implantable port can be in fluid communication with the implantable restriction device and the pump. The implantable restriction device is adjustable and configured to form a restriction in a patient, and the implantable port, if present, is configured to receive fluid from a fluid source external to the patient. The implantable MEMS pump has a fluid chamber disposed within a pump housing. The pump chamber has an inlet valve disposed between the fluid chamber and an inlet chamber, and an outlet valve disposed between the fluid chamber and an outlet chamber. The pump also includes a pumping membrane in fluid communication with the fluid chamber and an electrode adjacent the pumping membrane. The pumping membrane is configured to deflect in response to a voltage applied to the electrode. The deflection of the pumping membrane creates a pressure differential between the fluid chamber and the inlet and outlet chambers to control flow of fluid through the pump.

The inlet and outlet valves are configured to open and close in response to pressure changes in the fluid chamber. Fluid in the restriction system can move in a direction from the MEMS pump to the restriction device or in a direction from the restriction device to the MEMS pump. In one embodiment, the pump can be in fluid communication with the implantable port. The system can also include an implantable sensor in communication with the restriction device and configured to measure at least a pressure within the restriction device. The restriction system can optionally include a fluid reservoir in fluid communication with the pump. The fluid reservoir is configured to hold fluid and can be configured to hold in the range of approximately 0.1 to 20 ml of fluid.

The pump can be manually activated to move fluid either toward or away from the restriction device. Alternatively, the pump can be automatically activated, such as by techniques including timer control, or programmed to be activated in response to certain sensed parameters. In one embodiment, the implantable pump effects a pressure change within the restriction device in accordance with at least one of a detected event and a programmed schedule.

Further disclosed herein are methods for adjusting pressure in an implantable restriction device. In one embodiment, the method can include sensing a clinically relevant parameter, adjusting a pressure within the restriction device in response to the sensed clinically relevant parameter by activating a pump in fluid communication with the restriction device. In one embodiment, the pump can be a micro-electro-mechanical systems (MEMS) device effective to create pumping action to move fluid through the pump. The sensing of the clinically relevant parameter can be effected using an implantable sensor. The clinically relevant parameter can be a pressure, in which case, the implantable sensor is a pressure sensor. In such an embodiment, the sensed pressure is compared to a desired pressure range and the pressure within the restriction device is adjusted to be approximately within the desired pressure range if the sensed pressure is not within a desired pressure range. In one embodiment, the pump can be automatically activated, although other activation techniques, including manual activation, are also envisioned.

In yet another embodiment there is provided an implantable micro-electro-mechanical systems (MEMS) pump in fluid communication with a fluid source and fluid target, the MEMS pump being configured to selectively convey a fluid between the fluid source and the fluid target. The fluid source and the fluid target can be implanted within the body and/or be sites naturally present within the body. The fluid can be any fluid, including a fluid that is or contains one or more therapeutic and/or biologically active agents.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides systems and methods for forming a restriction in a patient. In general, the systems and methods allow the pressure or volume of fluid in a restriction device to be adjusted. The pressure or volume adjustment is effected by the use of an implantable pump. The implantable pump allows the pressure or volume of fluid in a restriction device to be adjusted without the need for fluid to be added from an external source.

Figure 1A:
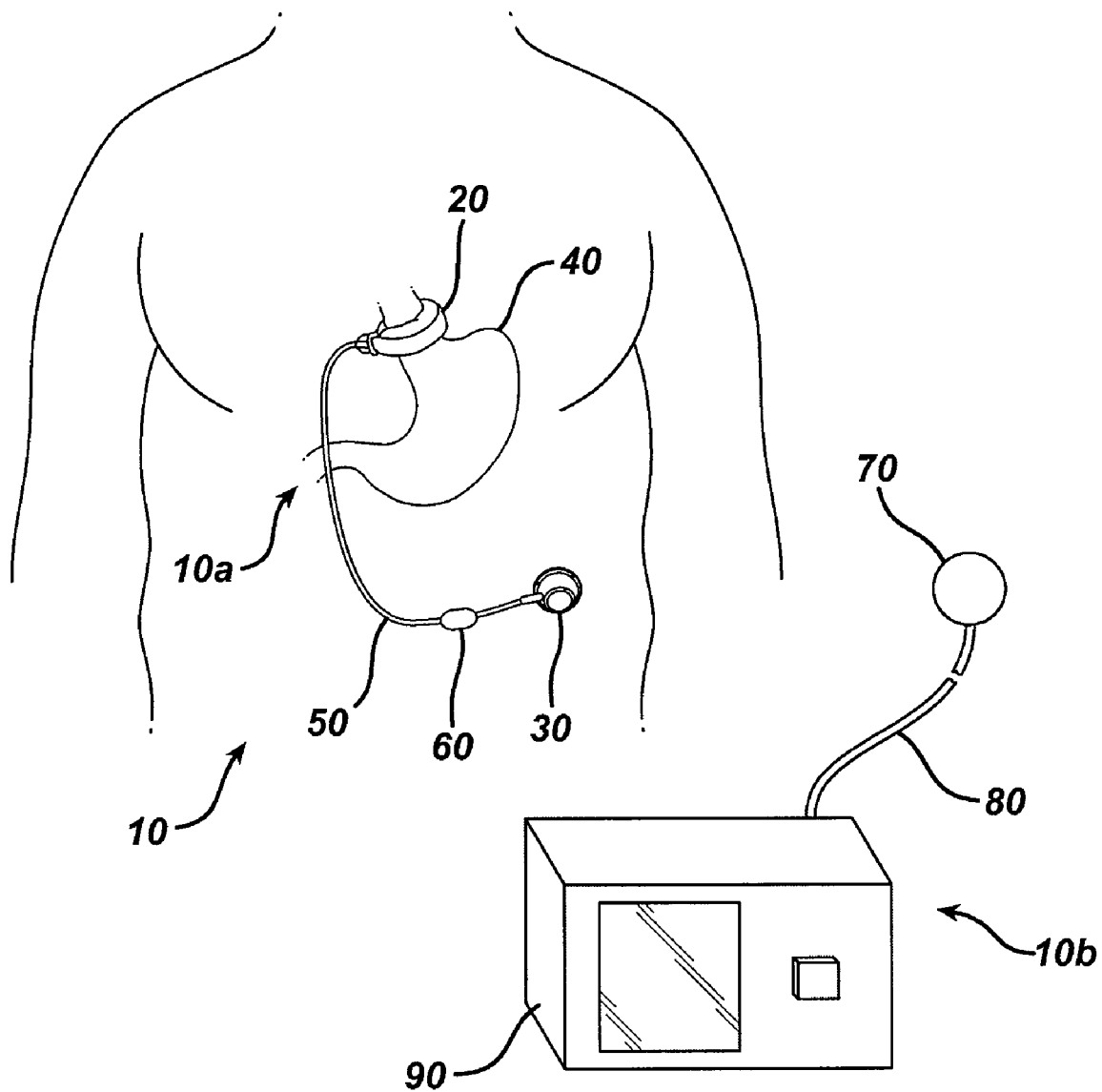
FIG. 1A is a schematic diagram of an embodiment of a food intake restriction system.
Figure 1B:
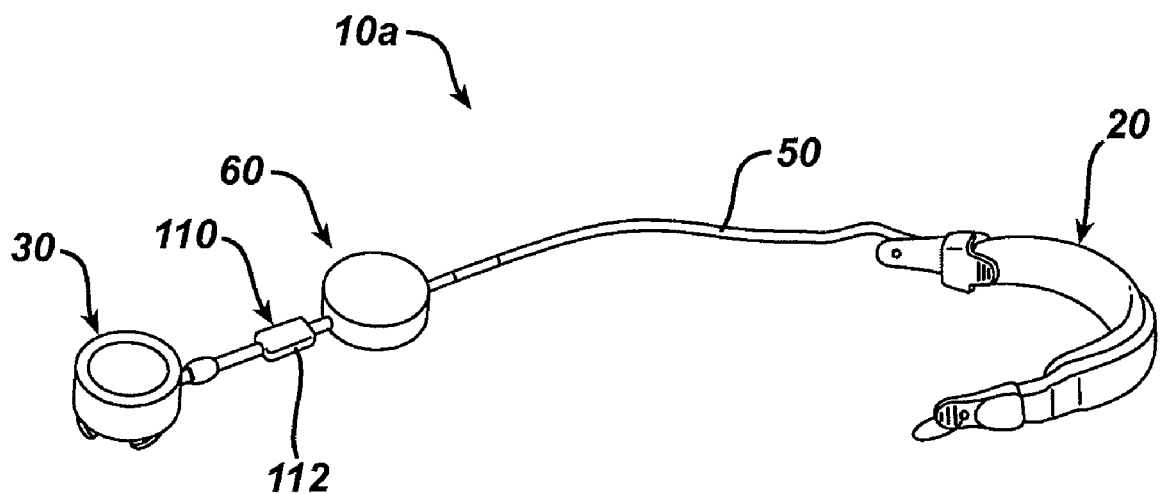
FIG. 1B is a perspective view of an embodiment of an implantable portion of the food intake restriction system of FIG. 1A.

While the present invention can be used with a variety of restriction systems known in the art, FIG. 1A illustrates one exemplary embodiment of a food intake restriction system 10 in use in a patient. As shown, the system 10 generally includes an implantable portion 10a and an external portion 10b. FIG. 1B illustrates the implantable portion 10a outside of a patient. The implantable portion 10a includes an adjustable gastric band 20 that is configured to be positioned around the upper portion of a patient's stomach 40, and an injection port housing 30 that is fluidly coupled to the adjustable gastric band 20, e.g., via a catheter 50.

The injection port housing 30 is adapted to allow fluid to be introduced into and removed from the gastric band 20 to thereby adjust the size of the band, and thus the pressure applied to the stomach. The injection port housing 30 can thus be implanted at a location within the body that is accessible through the tissue. Typically, injection ports are positioned in the lateral subcostal region of the patient's abdomen under the skin and layers of fatty tissue. Surgeons also typically implant injection ports on the sternum of the patient.

The internal portion 10a can also include a sensing or measuring device in fluid communication with the closed fluid circuit in the implantable portion 10a such that the measuring device can take measurements related to any parameter relevant to implantable restriction devices. Such clinically relevant parameters include, but are not limited to, temperature, pressure, changes in pressure, acoustic input, tissue impedance, changes in sensed tissue impedance, chemical composition, changes in chemical composition, pulse count, pulse width and amplitude. While the methods and devices discussed herein can relate to any sensed data parameter, in an exemplary embodiment, the measurements relate to pressure, and the methods and devices disclosed herein will be discussed in the context of measuring the fluid pressure of the closed fluid circuit. While the measuring device can have various configurations and it can be positioned anywhere along the internal portion 10a, including within the injection port housing 30, in the illustrated embodiment the measuring device is in the form of a pressure sensor that is disposed within a sensor housing 60 positioned adjacent to the injection port housing 30. The catheter 50 can include a first portion that is coupled between the gastric band 20 and the sensor housing 60, and a second portion that is coupled between the sensor housing 60 and the injection port housing 30.

In addition to sensing pressure of fluid within the internal portion 10a, pressure of fluid within the esophagus and/or the stomach 40 can also be sensed using any suitable device, such as an endoscopic manometer. By way of non-limiting example, such fluid pressure measurements can be compared against measured pressure of fluid within the internal portion 10a before, during, and/or after adjustment of pressure within the internal portion 10a. Other suitable uses for measured pressure within the esophagus and/or the stomach 40 will be appreciated by those skilled in the art.

As further shown in FIG. 1A, the external portion 10b generally includes a pressure reading device 70 that is configured to be positioned on the skin surface above the sensor housing 60 (which can be implanted beneath thick tissue, e.g., over 10 cm thick) to non-invasively communicate with the sensor housing 60 and thereby obtain pressure measurements. The pressure reading device 70 can optionally be electrically coupled (in this embodiment via an electrical cable assembly 80) to a control box 90 that can display the pressure measurements, or other data obtained from the pressure reading device 70.

FIG. 1B shows the implantable portion 10a in more detail. In the illustrated embodiment, the implantable portion 10a includes an adjustable gastric band 20, an injection port housing 30 that is fluidly coupled to the adjustable gastric band 20, a sensor housing 60, and a pump 110. The pump 110 can have a variety of configurations which will be discussed in more detail below. In the embodiment shown in FIG. 1B, the pump 110 is generally contained within a pump housing 112.

Figure 2A:
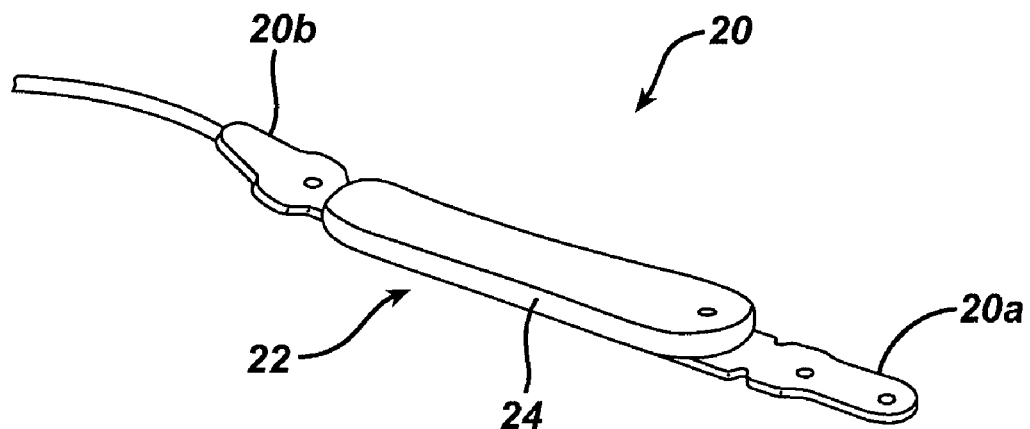
FIG. 2A is a perspective view of the food intake restriction device of FIG. 1A.

FIG. 2A shows the gastric band 20 in more detail. While the gastric band 20 can have a variety of configurations, and various gastric bands currently known in the art can be used with the present invention, in the illustrated embodiment the gastric band 20 has a generally elongate shape with a support structure 22 having first and second opposite ends 20a, 20b that can be secured to each other. Various mating techniques can be used to secure the ends 20a, 20b to one another. In the illustrated embodiment, the ends 20a, 20b are in the form of straps that mate together, with one laying on top of the other. The gastric band 20 can also include a variable volume member, such as an inflatable balloon 24, that is disposed or formed on one side of the support structure 22, and that is configured to be positioned adjacent to tissue. The balloon 24 can expand or contract against the outer wall of the stomach to form an adjustable stoma for controllably restricting food intake into the stomach.

A person skilled in the art will appreciate that the gastric band can have a variety of other configurations, moreover the various methods and devices disclosed herein have equal applicability to other types of implantable bands. For example, bands are used for the treatment of fecal incontinence, as described in U.S. Pat. No. 6,461,292 which is hereby incorporated herein by reference. Bands can also be used to treat urinary incontinence, as described in U.S. Patent Application 2003/0105385 which is hereby incorporated herein by reference. Bands can also be used to treat heartburn and/or acid reflux, as disclosed in U.S. Pat. No. 6,470,892 which is hereby incorporated herein by reference. Bands can also be used to treat impotence, as described in U.S. Patent Application 2003/0114729 which is hereby incorporated herein by reference.

Figure 2B:
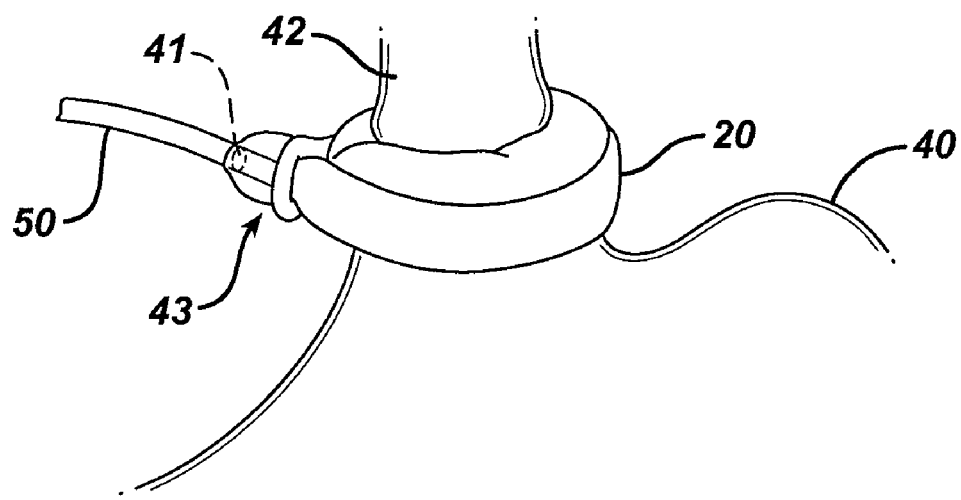
FIG. 2B is a schematic diagram of the food intake restriction device of FIG. 2A applied about the gastro-esophageal junction of a patient.

FIG. 2B shows the adjustable gastric band 20 applied about the gastro-esophageal junction of a patient. As shown, the band 20 at least substantially encloses the upper portion of the stomach 40 near the junction with the esophagus 42. After the band 20 is implanted, preferably in the deflated configuration wherein the band 20 contains little or no fluid, the band 20 can be inflated, e.g., using saline, to decrease the size of the stoma opening. A person skilled in the art will appreciate that various techniques, including mechanical and electrical techniques, can be used to adjust the band. FIG. 2B also shows an alternate location of a pressure sensor 41, disposed in a buckle 43 of the band 20.

Figure 3:
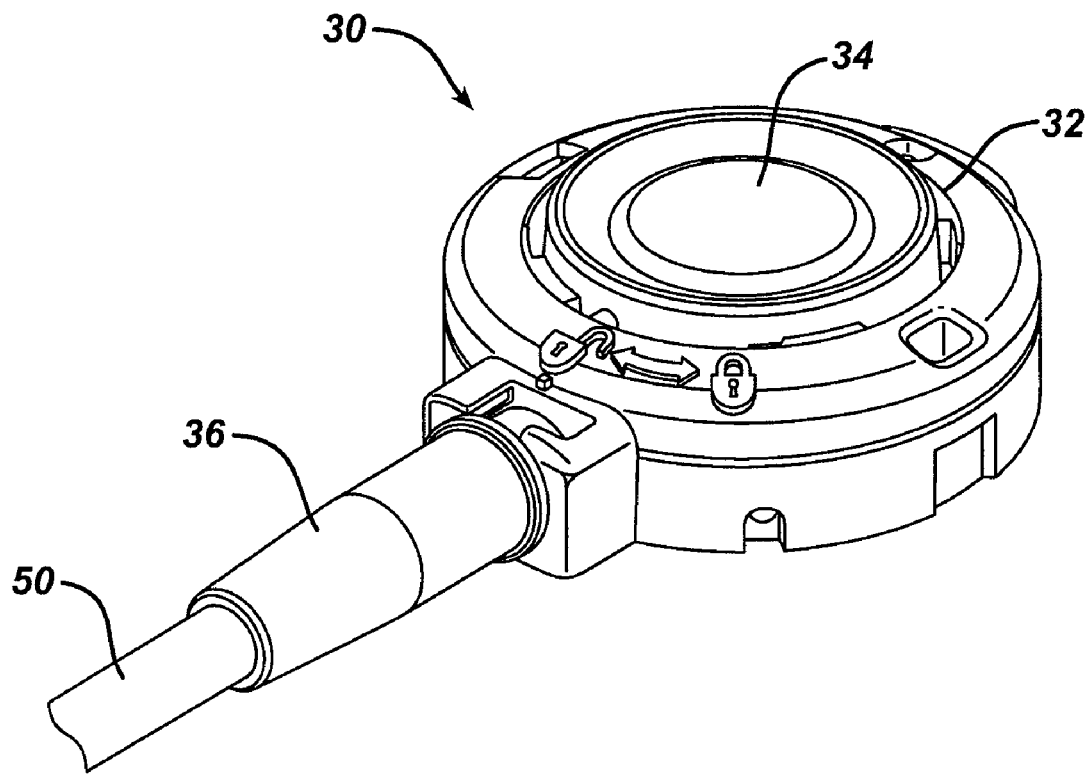
FIG. 3 is a perspective view of an embodiment of the injection port housing of FIG. 1A.

The fluid injection port housing 30 can also have a variety of configurations. In the embodiment shown in FIG. 3, the injection port housing 30 has a generally cylindrical shape with a distal or bottom surface and a perimeter wall extending proximally from the bottom surface and defining a proximal opening 32. The proximal opening 32 can include a needle-penetrable septum 34 extending there across and providing access to a fluid reservoir (not visible in FIG. 3) formed within the housing. The septum 34 is preferably placed in a proximal enough position such that the depth of the reservoir is sufficient enough to expose the open tip of a needle, such as a Huber needle, so that fluid transfer can take place. The septum 34 is preferably arranged so that it will self seal after being punctured by a needle and the needle is withdrawn. As further shown in FIG. 3, the port 30 can further include a catheter tube connection member 36 that is in fluid communication with the reservoir and that is configured to couple to a catheter (e.g., the catheter 50). A person skilled in the art will appreciate that the housing can be made from any number of materials, including stainless steel, titanium, or polymeric materials, and the septum 34 can likewise be made from any number of materials, including silicone.

Figure 4:
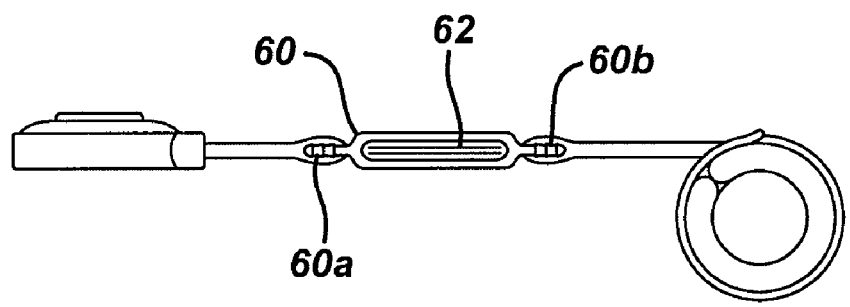
FIG. 4 is a perspective view of an embodiment of the sensor housing of FIG. 1A.

As indicated above, the system 10 can also include a pressure measuring device in communication with the closed fluid circuit and configured to measure pressure (e.g., fluid pressure) which corresponds to the amount of restriction applied by the adjustable gastric band 20 to the patient's stomach 40. Measuring the pressure enables a person (e.g., a physician, a nurse, a patient, etc.) to evaluate the efficacy and functionality of the restriction created by a band adjustment. In the illustrated embodiment, as shown in FIG. 4, the pressure measuring device is in the form of a pressure sensor 62 disposed within the sensor housing 60. The pressure measuring device can, however, be disposed anywhere within the closed hydraulic circuit of the implantable portion, and various exemplary locations and configurations are disclosed in more detail in commonly-owned U.S. Publication No. 2006/

0211913 entitled "Non-Invasive Pressure Measurement In a Fluid Adjustable Restrictive Device," filed on Mar. 7, 2006, and hereby incorporated by reference.

In general, the illustrated sensor housing 60 includes an inlet 60a and an outlet 60b that are in fluid communication with the fluid in the implantable portion 10a. An already-implanted catheter 50 can be retrofitted with the sensor housing 60, such as by severing the catheter 50 and inserting barbed connectors (or any other connectors, such as clamps, clips, adhesives, welding, etc.) into the severed ends of the catheter 50. The sensor 62 can be disposed within the housing 60 and be configured to respond to fluid pressure changes within the hydraulic circuit and convert the pressure changes into a usable form of data. The pressure sensor 62 disposed within the housing 60 can sense and monitor the adjusted state of the band statically or while fluid is being pumped.

While not shown, the pressure sensing system can also include a microcontroller, a TET/telemetry coil, and a capacitor. Optionally, the pressure sensing system can further comprise a temperature sensor (not shown). The microcontroller, TET/telemetry coil, and capacitor can be in communication via a circuit board (not shown) or any via any other suitable component(s). It will also be appreciated that TET/telemetry coil and capacitor may collectively form a tuned tank circuit for receiving power from external portion, and transmitting the pressure measurement to the pressure reading device.

Various pressure sensors known in the art can be used, such as a wireless pressure sensor provided by CardioMEMS, Inc. of Atlanta, Ga., though a suitable MEMS pressure sensor may be obtained from any other source, including but not limited to Integrated Sensing Systems (ISSYS), and Remon Medical. One exemplary MEMS pressure sensor is described in U.S. Pat. No. 6,855,115, the disclosure of which is incorporated by reference herein for illustrative purposes only. It will also be appreciated that suitable pressure sensors may include, but are not limited to, capacitive, piezoresistive, silicon strain gauge, or ultrasonic (acoustic) pressure sensors, as well as various other devices capable of measuring pressure.

The pressure reading device 70 can also have a variety of configurations, and one exemplary pressure reading device is disclosed in more detail in commonly-owned U.S. Patent Application Publication No. 2006/0189888 and U.S. Patent Application Publication No. 2006/0199997, each of which is hereby incorporated by reference in its entirety. In general, the pressure reading device 70 can non-invasively measure the pressure of the fluid within implanted portion even when the injection port housing 30 or sensor housing 60 is implanted beneath thick (at least over 10 centimeters) subcutaneous fat tissue. The physician may hold pressure-reading device 70 against the patient's skin near the location of sensor and observe the pressure reading on a display on the control box 90. The pressure reading device 70 can also be removably attached to the patient, such as during a prolonged examination, using straps, adhesives, and other well-known methods. The pressure reading device 70 can operate through conventional cloth or paper surgical drapes, and can also include a disposable cover (not shown) that may be replaced for each patient.

Figure 5:
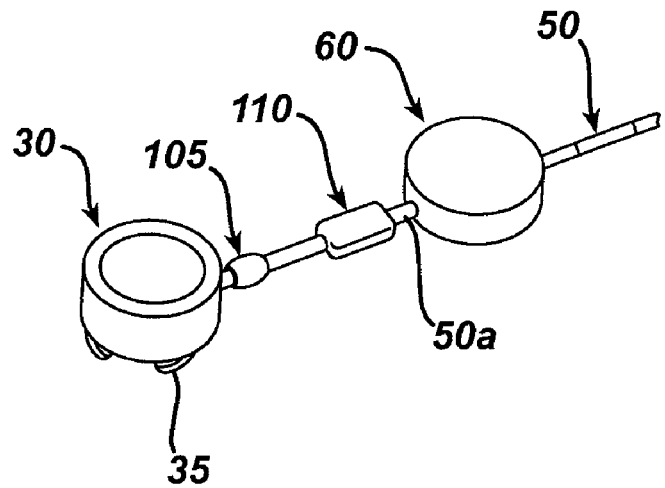
FIG. 5 is a perspective view of an implantable portion of the food intake restriction system according to one embodiment of the invention.

FIG. 5 illustrates one embodiment of the proximal end of the implantable portion 10a (FIGS. 1A and 1B) of the implantable restriction system 10. As shown, the proximal end of the implantable portion 10a includes an injection port housing 30, which is in fluid communication with a reservoir 105 and a pump 110. The proximal end may also include a sensor housing 60, as well as one or more sensor/power leads 101. Conduit 50a provides fluid communication between the individual components of the proximal end of the implantable portion 10a. Catheter 50 provides fluid communication between the proximal end of the implantable portion 10a shown in FIG. 5 and downstream restriction device 20 (FIG. 1B). Although the components shown in FIG. 5 are shown in an inline configuration, one skilled in the art will appreciate that the components can be connected in any order and in any configuration, i.e., in a T configuration or a Y configuration, for example.

As shown in FIG. 5, the injection port housing 30, if present, can optionally include an anchoring device, such as hooks 35, that can be used to anchor the injection port housing 30 within the patient's body. Although FIG. 5 shows that the housing 30 is arranged in line with the reservoir 105, the pump 110 and the sensor housing 60, the housing 30 can be connected to the other components and conduit 50a in other ways, i.e., in a T configuration or a Y configuration, for example. The injection port housing 30 itself is optional because the implantable restriction system 10a (FIG. 1B) can be filled with fluid prior to implantation or at the time of implantation. The pressure in the downstream restriction device 20 (FIG. 1B) can then be adjusted using the pump 110 to move fluid into or out of the restriction device 20.

Reservoir 105 provides an optional means for holding an additional supply of fluid. For example, the reservoir 105 can contain 0.1-20 ml of fluid. As shown, the reservoir 105 can be a portion of conduit 50a with a larger diameter than the nominal diameter of the conduit 50a. Various other configurations can be used to provide a reservoir 105, such as separate reservoir components connected to, and in fluid communication with, the conduit 50a or any other components, i.e., the injection port housing 30, the pump 110 or the sensor housing 60. Although FIG. 5 shows that the reservoir 105 is arranged in line between the pump 110 and the injection port housing 60, one skilled in the art will appreciate that the reservoir 105 can be connected to the other components and conduit 50a in other ways, i.e., in a r configuration or a Y configuration, for example. It will also be appreciated that the reservoir 105 need not necessarily contain enough fluid to fill and empty the entire band 20 (FIGS. 1A and 1B). For example, during the first fills of the band 20, fluid may be delivered via an injection through the injection port housing 30. During this time the pump 110 can be retained in an open position. Alternatively, the reservoir 105 can be filled and then the fluid can be delivered to the band 20 by the pump 110. Once the band 20 is at functional fullness, i.e., occluding the stomach enough to cause a restriction of intake, the reservoir 105 can be filled with enough fluid to accommodate future fill and adjustment needs without the need to add additional fluid via an injection port housing 30. One skilled in the art will appreciate that the reservoir 105 is optional, and in an embodiment without reservoir 105, not shown, the conduit 50a can optionally contain enough fluid to allow adjustments to the amount of fluid in the band 20.

The embodiment shown in FIG. 5 includes an optional sensor housing 60 that is disposed in fluid communication with the components of the proximal end of the implantable portion 10a (FIG. 1B). Although FIG. 5 shows that the sensor housing 60 is arranged inline with the catheter 50 and the conduit 50a, one skilled in the art will appreciate that the sensor housing 60 can be connected to the other components in other ways, i.e., in a T configuration or a Y configuration, for example. Alternatively, a sensor can be placed in other locations in the system, such as on the band itself. Sensor/power leads 101 can provide a connection between the sensor housing 60 and the pump 110 to supply energy to the pump, as will be discussed in more detail below.

The implantable pump 110 functions to move fluid into and out of the band 20 to increase or decrease pressure within the band as needed. Although the pump can have a variety of configurations, in one example the pump is based upon micro-electro-mechanical systems (MEMS) technology as discussed in more detail below. In general, MEMS technology can be characterized by the use of elements on a sub-millimeter scale. The use of MEMS technology to form an implantable pump 110 provides a number of advantages, such as small size, low voltage requirements, and simplicity in terms of the number of moving parts. Additional advantages include reduced manufacturing costs, improved performance, high accuracy, high precision, fast response time, and configurations that cannot be achieved on a larger scale.

Figure 6:
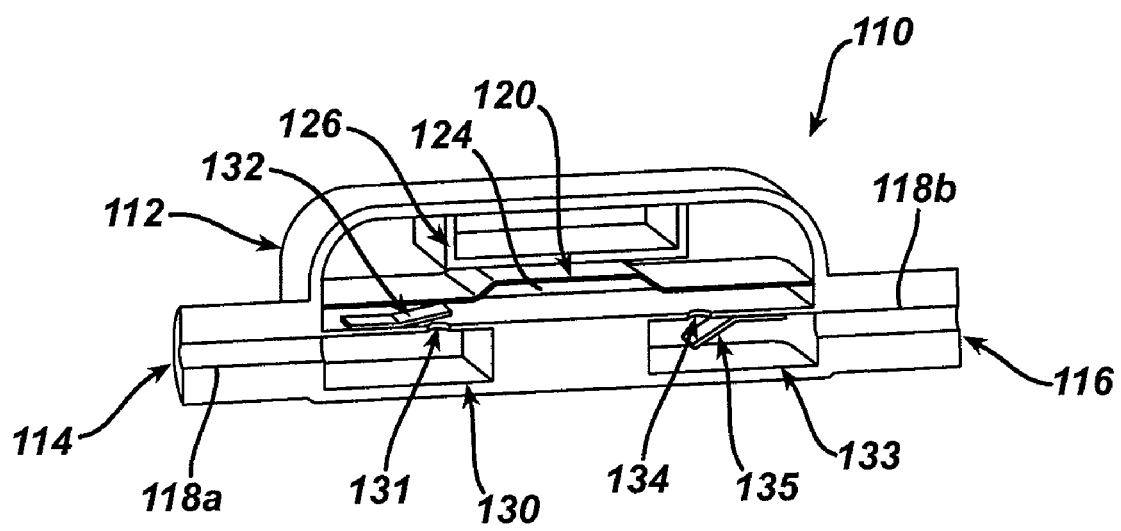
FIG. 6 is a sectional view of an exemplary embodiment of an implantable MEMS pump.

FIG. 6 illustrates one exemplary embodiment of a MEMS pump. As shown, the pump 110 is generally contained within pump housing 112 having a proximal end 114 and a distal end 116, each of which include an inner lumen 118a, 118b. The inner lumens 118a, 118b are disposed in fluid communication with the components of the proximal end of the implantable portion 10a (FIG. 1B). The pump housing 112 may optionally be formed integrally with conduit 50a (FIG. 5) such that the pump 110 is in fluid communication with catheter 50 and downstream restriction device 20. As shown, the pump 110 can include an electrode 126 adjacent a pumping membrane 122 disposed in fluid communication with a fluid chamber 124. The pump 110 can also include an inlet chamber 130 and an outlet chamber 133. The inlet chamber 130 can be disposed in fluid communication with the fluid chamber 124 via inlet hole 131. Likewise, the outlet chamber 133 can be disposed in fluid communication with the fluid chamber 124 via outlet hole 134. The pump can also include an inlet valve 132 and an outlet valve 135. In use, as will be explained in more detail below, the membrane 122 is configured to deflect in response to a voltage applied to electrode 126, thereby creating a pressure differential between the fluid chamber 124 and the inlet chamber 130 and/or outlet chamber. The pump housing 112 can have a variety of configurations, but in one exemplary embodiment it is formed in line with the conduit 50a. The shape and size of the pump housing 112, as well as the materials used to form the housing 112 and its interior components, can vary upon the intended use. MEMS devices are typically made of silicone but can also be made of polymers, metals or shape memory alloys. In certain exemplary embodiments, the pump housing 112 can be formed from a biocompatible polymer, such as silicone or latex. Other suitable biocompatible elastomers and polymers include, by way of non-limiting example, synthetic polyisoprene, chloroprene, fluoroelastomer, nitrile, fluorosilicone, polyvinylidene difluoride (PVDF), and liquid crystal polymer (LCP).

A person skilled in the art will appreciate that the materials can be selected to obtain the desired mechanical properties. While not shown, the housing 112 can also include other features to facilitate attachment thereof to a medical device, a fluid source, etc.

One skilled in the art will appreciate that a microfluidic pump device can be formed of two layers of an elastomeric material. One layer contains channels for flowing liquids (i.e., the flow layer) while the other layer (i.e., the control layer) contains channels that deflect the membrane valve into the flow channel and stop liquid flow when pressurized with air/fluid. One skilled in the art will also appreciate that the valves can be incorporated into the MEMS die.

The pump 110 can be configured in a variety of configurations. In the illustrated embodiment, the pump housing 112 includes a series of fluid chambers. The main fluid chamber 124 is formed within the pump housing 112 and is in fluid communication with pumping membrane 120. Further, the main fluid chamber 124 is disposed in fluid communication with an inlet chamber 130 and an outlet chamber 133 via an inlet hole 131 and an outlet hole 134. The inlet chamber 130 and the outlet chamber 133 are separated from the main fluid chamber 124 by an inlet valve 132 and an outlet valve 135. The valves can have a variety of configurations. In the illustrated embodiment the inlet valve 132 and outlet valve 135 are formed as leaf springs that are biased in a closed position, i.e., biased in a position preventing fluid flow through the holes 131 and 134. The inlet valve 132 can be disposed within the main fluid chamber 124 and allows fluid to pass from the inlet chamber 130 to the main fluid chamber 124. The outlet valve can be disposed within the outlet chamber 133 and allows fluid to pass from the main fluid chamber 124 to the outlet chamber 133. A person skilled in the art will appreciate that the locations of the inlet valve 132 and the outlet valve 135 are interchangeable. A person skilled in the art will also appreciate that one or both of the inlet chamber 130 and outlet chamber 133 are optional. For example, one or both of the inner lumens 118a, 118b can be connected directly to the main fluid chamber 124. In such a configuration, the inlet valve 132 and/or the outlet valve 135 can be formed within the inner lumens 118a, and 118b, for example. As discussed above, the elements of the pump 110, including valves 132, 135 can be formed on a sub-millimeter scale.

The pumping membrane 120 can also be configured in a variety of configurations. In the illustrated embodiment, the pumping membrane 120 is disposed within the housing 112 and is disposed in fluid communication with the main fluid chamber 124. The pumping membrane 120 can be formed from a suitable biocompatible polymer or metal that is responsive to an electric field produced by the application of a voltage to an electrode 126. The electrode 126 can also have a variety of configurations. In the illustrated embodiment, the electrode 126 is formed within the pump housing 112 and is disposed adjacent the pumping membrane 120. A person skilled in the art will appreciate that the electrode 126 can be disposed in any location. For example, the electrode 126 can be disposed in the lower surface of the pumping chamber 124. A person skilled in the art will also appreciate that the electrode 126 should be made of corrosion resistant materials such as platinum or other noble metals to survive harsh fluids such as saline.

One of the advantages of using MEMS technology to form the pump is the small overall size and the small volume adjustments that can be attained. By way of example, the largest dimension of the entire pump can be less than about 5 mm including control electronics. Although the pump can be designed to attain any desired flow rate, the flow rate can be as low as 0.1 ml/minute to 0.5 ml/minute. The total volume change required to effect the desired pressure adjustment can be delivered by operation of the pump at such a flow rate. For example, the total volume delivered to the band 20 can be less than 1 ml for a given desired adjustment.

As shown, the electrode 126 is disposed adjacent the pumping membrane 120. The position of the pumping membrane 120 can be controlled by a voltage applied to the electrode 126. A person skilled in the art will appreciate that the applied voltage can vary depending on numerous factors, as discussed below, and is generally in the range of about 2 to about 200 volts. The voltage applied to the electrode can be dependent on a number of factors such as, for example, switching speed, required switching forces or deflection, and reliability of the MEMS device. For example, higher switching speeds of approximately 25 microseconds may require voltages of approximately 10-15 volts while slower switching speeds typically require voltages less than approximately 5V. In an alternate example, high voltage electrostatic actuators can be used, for which the voltage can be in the range of approximately 10V-300V. The electrode 126 can be coupled to a battery or other energy source. Where the pump 110 is adapted to be implanted within the patient, the electrode 126 can be coupled to a transformer that is adapted to be subcutaneously implanted and that is adapted to store energy and/or receive energy from an external source located outside of the patient's body. For example, the transformer or power source can be contained in the sensor housing 60 and sensor/power leads (not shown) can deliver energy to the electrode 126. Alternatively, energy can be supplied by an external device (e.g., the reading device 70 shown in FIG. 1A) that can transcutaneously deliver energy to the sensor housing 60 (FIG. 5), e.g., when the external device is moved in proximity of the sensor housing 60. The external device can be mobile (e.g., a wand or hand-held unit that can be waved or otherwise placed in proximity of the sensor housing 60) or stationary (e.g., a bedside, desk-mounted, or car-mounted box that the patient can move near).

Figure 7A:
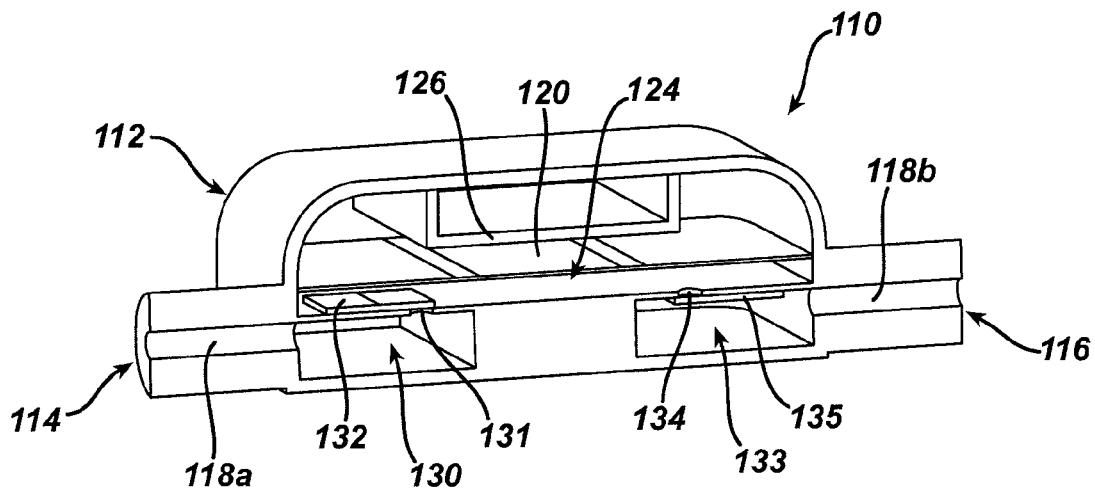
FIG. 7A is a sectional view of the pump of FIG. 6 in its rest state.
Figure 7B:
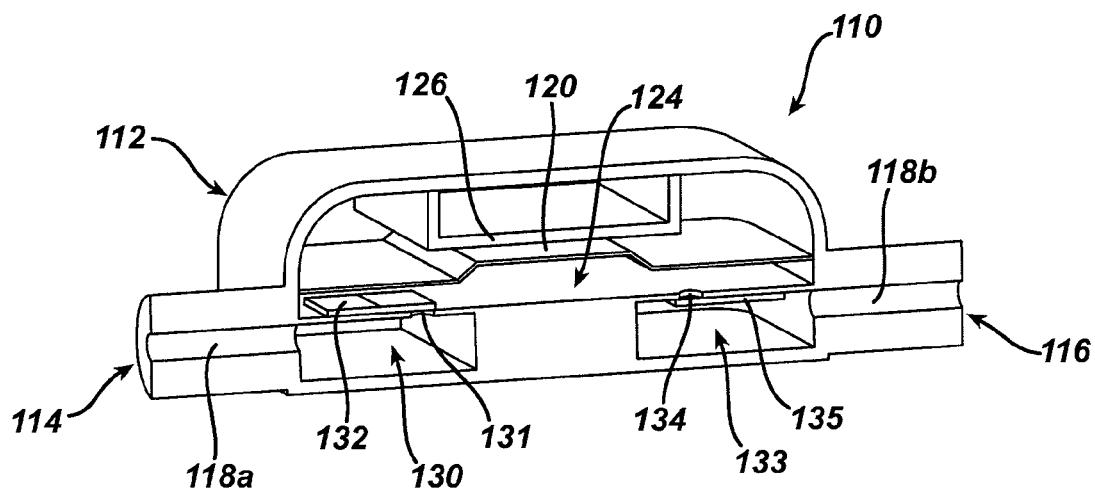
FIG. 7B is a sectional view of the pump of FIG. 6 showing deflection of the membrane when current is applied to the electrode.

FIGS. 7A-7D illustrate one exemplary method for creating a pressure differential within the pump 110 to move fluid through the pump 110. In an exemplary embodiment the pump moves fluid in a distal direction toward band (FIG. 1B), which would be located distally of the pump 110. FIG. 7A shows the pump 110 in its rest state, with the pumping membrane 120 substantially undeflected and both the inlet valve 132 and the outlet valve 135 closed. When a voltage is applied to the electrode 126, the pumping membrane 120 deflects and is drawn toward the electrode 126 to the extent that material properties will allow it to be drawn, as shown in FIG. 7B. Alternatively, a hard stop (not shown) can limit the travel of the membrane 120 to precisely control its movement. A person skilled in the art will appreciate that when the electrode 126 is disposed in other locations, as discussed above, the pumping membrane can alternatively be repelled from the electrode.

Figure 7C:
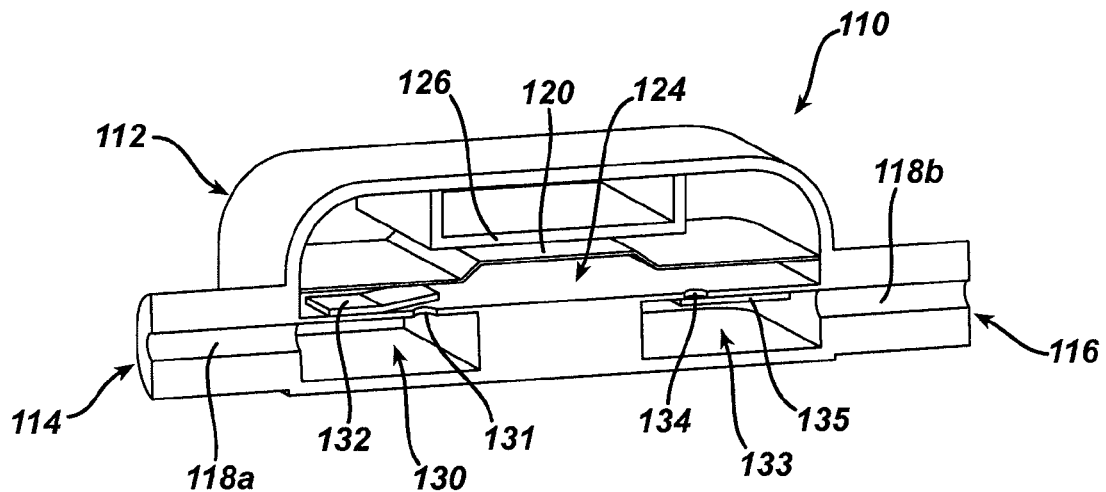
FIG. 7C is a sectional view of the pump of FIG. 6 with the inlet valve open in response to a pressure change in the fluid chamber.
Figure 7D:
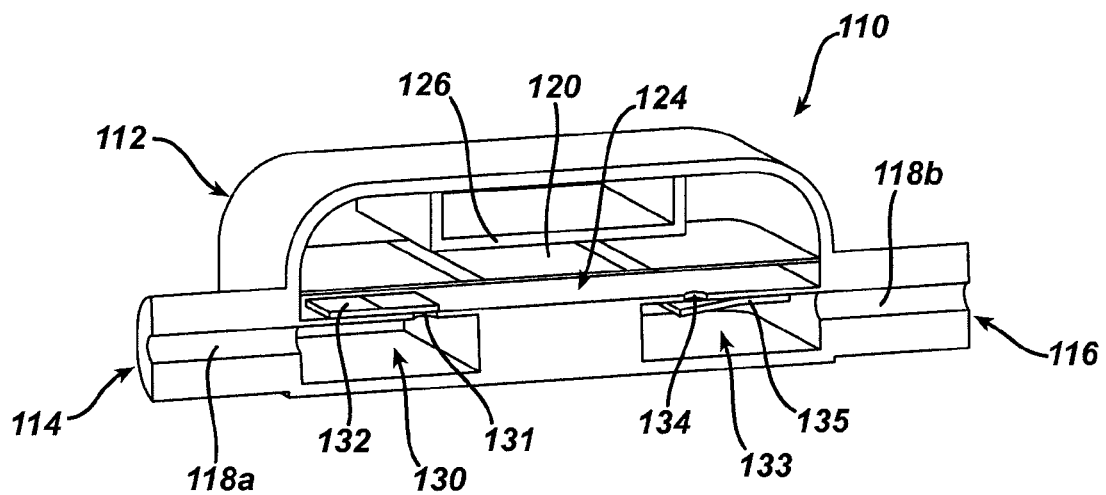
FIG. 7D is a sectional view of the pump of FIG. 6 with the outlet valve open in response to pressure change in the fluid chamber.

The increase in volume in the main fluid chamber 124 causes a pressure drop relative to the pressures in the inlet and outlet chambers 130, 133. As shown in FIG. 7C, the differential in pressures between the inlet chamber 130 and the main fluid chamber 124 causes the inlet valve 132 to open, allowing fluid to move into the main fluid chamber 124 until pressures equalize. During this time, the pressure differential between the main fluid chamber 124 and the outlet chamber 133 forces the outlet valve 135 to remain closed. Once the fluid from the inlet chamber 130 has filled the main fluid chamber 124, the voltage applied to the electrode 126 is reduced, allowing the pumping membrane 120 to return to its rest state. The decrease in volume in the main fluid chamber 124 as a result of the movement of the pumping membrane 120 back to its rest state causes a pressure rise in the main fluid chamber 124 relative to the pressures in the inlet and outlet chambers 130, 133. As shown in FIG. 7D, the differential in pressures between the main fluid chamber 124 and the outlet chamber 130 causes the outlet valve 135 to open, allowing fluid to move into the outlet chamber 133 until pressures equalize. During this time, the pressure differential between the main fluid chamber 124 and the inlet chamber 130 forces the inlet valve 132 to remain closed. The process illustrated in FIGS. 7A-7D can be repeated, as necessary, to continue the pumping action.

Figure 8:
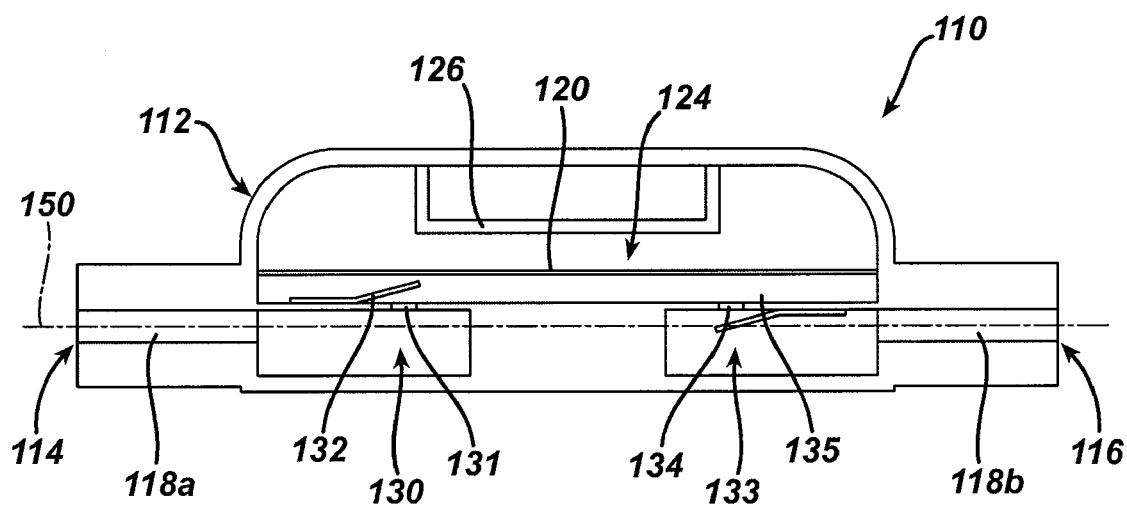
FIG. 8 is a schematic view of the of the pump of FIG. 6 showing the path of fluid through the pump.

FIG. 8 illustrates the path 150 of fluid through the pump 110. In the illustrated embodiment, the pump moves fluid in a distal direction toward band (FIG. 1B), which would be located distally of the pump 110. Fluid moves from the inner lumen 118a at the proximal end 114 of the pump 110, into the inlet chamber 130, and through the inlet valve 132 into the main fluid chamber 124. Fluid then passes through the outlet valve 135 into the outlet chamber 130 and through the inner lumen 118b of the distal end 116 of the pump 110. A person skilled in the art will appreciate that the arrangement of fluid chambers and valves can be modified, as needed, to allow fluid to move in a proximal direction away from the band (FIG. 1B). For example, since the band is the high pressure side of the system, a return valve may simply be opened to allow fluid to be expelled from the band. Alternatively, a second MEMS pump may be oriented in the opposite direction as the first to pump fluid away from the band.

The present invention also provides a method of adjusting pressure in an implantable restriction device system 10. In one embodiment, the method can include sensing a clinically relevant parameter and adjusting a pressure within the restriction device in response to the sensed clinically relevant parameter by activating a pump in fluid communication with the restriction device 20. The pump can be a MEMS-based pump of the type described with respect to FIGS. 6-8. That is, the pump can be a micro-electro-mechanical systems device effective to create pumping action to move fluid through the pump. The clinically relevant parameter can be sensed using an implantable sensor.

In one embodiment, the sensed clinically relevant parameter is a pressure, although it is understood that it can include any one of the other parameters identified above, as well as other clinically relevant parameters. In this embodiment, the pressure can be sensed using an implantable pressure sensor 62, as discussed above. The method can include sensing a pressure in an implanted restriction device 10a, comparing the sensed pressure to a desired pressure (including a desired pressure range), and adjusting the pressure within the restriction device 10a to be approximately equal to the desired pressure (or desired pressure range) if the sensed pressure is not equal to the desired pressure (or desired pressure range) by activating a pump in fluid communication with the restriction device 20 to achieve a desired pressure (or desired pressure range) in the restriction device.

In one embodiment, activation of the pump 110 could automatically occur if the sensed clinically relevant parameter (e.g., pressure, etc.) in the band 30 were higher than a desired value or range, in which case fluid could be pumped out of the band 30 to reduce the pressure. Conversely, if the sensed parameter in the band 30 were lower than a desired value or range, the fluid could be pumped into the band (e.g., from a reservoir or from an implanted catheter) until a desired target for the parameter is achieved. In yet another configuration, if a sensed clinically relevant parameter (e.g., absolute pressure at a given duration, pressure gradient, etc.) in the band 30 which correlates with undesirable eating habits was measured, the fluid could be pumped into the band (e.g., from a reservoir or from an implanted catheter) until a sufficient restriction was created. This restriction would provide feedback to the patient (which can be immediate or delayed) to stop eating by inducing a physiologic response (e.g., vomiting, etc.). The restriction would be sustained in place until a triggering event (e.g., elapsed time) occurred to return the system to a normal operating state. For safety purposes, an override which can be activated by the patient or other caregiver may be provided. This override may be activated through a function in the external portion 10b of the food intake restriction system 10. Other techniques for automatic actuation can be used such as timer control, or the system can be programmed to activate the pump in response to certain sensed parameters or events, or according to a programmed schedule. For example, the implantable pump can effect a pressure increase within the restriction device (i.e., move fluid towards the restriction device) when a patient is determined to be eating, or when the patient is awake (or during selected hours of a day) and effect a pressure decrease within the restriction device (i.e., move fluid away from the restriction device) when the patient is asleep (or during other selected hours of a day). Those skilled in the art will appreciate that the programmed schedule can be based on a multitude of factors including type of day (e.g., holidays, weekday, weekend), anticipated patient activities, and the like. Those skilled in the art will appreciate that the pressure in the band 30 can be controlled using closed-loop methods such as PID (proportional-integral-derivative) control schemes or other appropriate methods including digital control schemes.

One skilled in the art will appreciate that certain safety features may be built into the pump design to provide contingencies in the event of a malfunction or a loss of power. By way of example, if a power outage (or malfunction) is detected, or if the remaining power falls below a predetermined threshold, the system can be configured to default to a relaxed state in which the restriction is relaxed and/or opened until the power level is restored or the malfunction corrected.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used system is obtained and if necessary cleaned. The system can then be sterilized by any known and suitable technique, including ethylene oxide sterilization. In one sterilization technique, the system is placed in a closed and sealed container, such as a plastic or TYVEK bag. The container and system are then placed in a field of radiation that can penetrate the container, such as gamma radiation, x-rays, or high-energy electrons. The radiation kills bacteria on the system and in the container. The sterilized system can then be stored in the sterile container. The sealed container keeps the system sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A restriction system for forming a restriction in a patient, comprising:
   an implantable restriction device that is adjustable and configured to form a restriction in a patient; and
   an implantable micro-electro-mechanical systems (MEMS) pump in fluid communication with the restriction device;
   the system being configured to default to a state in which the restriction is at least one of relaxed or opened in the event of a malfunction or a loss of power.

2. The system of claim 1, further comprising an implantable port configured to receive fluid from a fluid source external to the patient wherein the implantable port is in fluid communication with the implantable restriction device and the pump.

3. The system of claim 1, further comprising an implantable sensor in communication with the restriction device.

4. The system of claim 3, wherein the implantable sensor is configured to measure at least a pressure within the restriction device.

5. The system of claim 1, wherein the MEMS pump comprises:
   a pump housing;
   a fluid chamber disposed within the pump housing and having an inlet valve disposed between the fluid chamber and an inlet chamber, and an outlet valve disposed between the fluid chamber and an outlet chamber;
   a pumping membrane in fluid communication with the fluid chamber; and
   an electrode adjacent the pumping membrane,
   wherein the pumping membrane is configured to deflect in response to a voltage applied to the electrode creating a pressure differential between the fluid chamber and the inlet and outlet chambers to control flow of a fluid through the pump.

6. The system of claim 5, wherein the inlet and outlet valves are configured to open and close in response to pressure changes in the fluid chamber.

7. The system of claim 5, wherein fluid moves in a direction from the MEMS pump to the restriction device.

8. The system of claim 5, wherein fluid moves in a direction from the restriction device to the MEMS pump.

9. The system of claim 1, wherein the implantable pump effects a pressure change within the restriction device in accordance with at least one of a detected event and a programmed schedule.

10. The system of claim 1, further comprising a fluid reservoir in fluid communication with the MEMS pump.

11. The system of claim 10, wherein the fluid reservoir is configured to hold in the range of approximately 0.1 to 20 ml of fluid.

12. The system of claim 1, wherein the pump serves as a valve that is able to selectively control the passage of fluid by permitting, preventing, or limiting the passage of fluid.

13. An implantable medical device, comprising:
   an implantable micro-electro-mechanical systems (MEMS) pump in fluid communication with a fluid source and fluid target, the MEMS pump being configured to selectively convey a fluid between the fluid source and the fluid target;
   the pump being configured to default to a state in which the pump permits fluid flow between the fluid target and the fluid source in the event of a malfunction or a loss of power.

* * * * *